United States Patent
Werner et al.

(10) Patent No.: US 10,118,923 B2
(45) Date of Patent: *Nov. 6, 2018

(54) COMPOSITIONS AND METHODS FOR INHIBITING KINASES

(71) Applicant: Inhibikase Therapeutics, Inc., Atlanta, GA (US)

(72) Inventors: Milton H. Werner, Marietta, GA (US); Terence A. Kelly, Ridgefield, CT (US)

(73) Assignee: Inhibikase Therapeutics, Inc., Atlanta, GA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/805,693

(22) Filed: Nov. 7, 2017

(65) Prior Publication Data
US 2018/0057488 A1 Mar. 1, 2018

Related U.S. Application Data

(63) Continuation of application No. 15/136,497, filed on Apr. 22, 2016, now Pat. No. 9,828,370.

(60) Provisional application No. 62/182,955, filed on Jun. 22, 2015, provisional application No. 62/151,659, filed on Apr. 23, 2015.

(51) Int. Cl.
| | |
|---|---|
| *C07D 403/14* | (2006.01) |
| *C07D 417/14* | (2006.01) |
| *C07D 401/14* | (2006.01) |
| *A61K 31/506* | (2006.01) |
| *A61K 45/06* | (2006.01) |
| *C07D 413/14* | (2006.01) |

(52) U.S. Cl.
CPC .......... *C07D 417/14* (2013.01); *A61K 31/506* (2013.01); *A61K 45/06* (2013.01); *C07D 401/14* (2013.01); *C07D 403/14* (2013.01); *C07D 413/14* (2013.01); *A61K 2300/00* (2013.01); *Y02A 50/393* (2018.01); *Y02A 50/467* (2018.01); *Y02A 50/473* (2018.01); *Y02A 50/475* (2018.01); *Y02A 50/481* (2018.01)

(58) Field of Classification Search
CPC ... C07D 401/14; C07D 403/14; A61K 31/506
USPC ...................... 544/295; 514/252.18
See application file for complete search history.

(56) References Cited

U.S. PATENT DOCUMENTS 9,828,370 B2 * 11/2017 Werner ............... C07D 417/14
2010/0249122 A1 9/2010 Kalman

FOREIGN PATENT DOCUMENTS

WO WO-2008/070350 A2 6/2008
WO WO-2008/079460 A2 7/2008

OTHER PUBLICATIONS

Bosseray, et al., "What's new in vaccines against herpes simplex infections?" Pathol Biol (Paris), 50(8): 483-492 (2002). (Abstract).
Douglas, Jr., "Introduction to Viral Diseases," Cecil Textbook of Medicine, 20(2): 1739-1747 (1996).
Goff, "Intracellular trafficking of retroviral genomes during the early phase of infection: viral exploitation of cellular pathways," J Gene Med, 3(6): 517-528 (2001). (Abstract).
Gura, "Systems for Identifying New Drugs are Often Faulty," Science, 278(5340): 1041-1042 (1997).
Johnson, et al., "Relationships between drug activity in NCI preclinical in vitro and in vivo models and early clinical trials," Br J Cancer, 84(10): 1424-1431 (2001).
Napier et al., "Low Doses of Imatinib Induce Myelopoiesis and Enhance Host Anti-microbial Immunity," Plos Pathog, 1-27 (Mar. 30, 2015).
Pearce, et al., "Failure modes in anticancer drug discover and development," Cancer Drug Design and Discovery: 424-435 (2008).
Razonable, et al., "Herpesvirus infections in transplant recipients: current challenges in the clinical management of cytomegalovirus and Epstein-Barr virus infections," Herpes, 10(3): 60-65 (2003). (Abstract).
Simone, "Oncology: Introduction," Cecil Textbook of Medicine, 20(1): 1004-1010 (1996).

* cited by examiner

*Primary Examiner* — Deepak R Rao
(74) *Attorney, Agent, or Firm* — Foley Hoag LLP; David P. Halstead; Lucas P. Watkins

(57) ABSTRACT

The present invention provides compounds for the prevention or treatment of cancer or a bacterial or viral infection. Additionally, the present invention provides compositions and methods for using these compounds and compositions in the prevention or treatment of cancer or a bacterial or viral infection in a subject.

13 Claims, 9 Drawing Sheets

COMPOSITIONS AND METHODS FOR INHIBITING KINASES

PRIORITY CLAIM

This application is a continuation of U.S. patent application Ser. No. 15/136,497, filed Apr. 22, 2016, which claims the benefit of, and priority to, U.S. Provisional Patent Application No. 62/182,955, filed Jun. 22, 2015, and U.S. Provisional Patent Application No. 62/151,659, filed Apr. 23, 2015. The disclosure of each of these applications is hereby incorporated by reference herein in its entirety.

STATEMENT REGARDING FEDERALLY SPONSORED RESEARCH OR DEVELOPMENT

This invention was made with government support under Contract No. 1R43AI103982-01A1 awarded by The National Institutes of Health. The government has certain rights in the invention.

BACKGROUND OF THE INVENTION

Anti-Infective Agents

Abelson-family tyrosine kinases (ATKs) are host targets that can be inhibited by small molecules (ATKis) to create anti-cancer and anti-infective therapeutics. When applied to treat infectious diseases in vitro and in vivo, more than 20 human bacterial viral, fungal and parasitic pathogens have been shown to be susceptible to ATK inhibition. Host ATKs are co-opted by a pathogen to enter, reproduce or exit host cells, accounting for the antimicrobial effects of ATKis. Because the targets of these therapeutics to treat infectious disease overlap with the targets for certain types of cancer, the same medications for infectious disease can be applied to treat cancer at the same dose.

For infectious disease, this strategy has been applied to treat the cause of Progressive Multifocal Leukoencephalopathy (PML) a fatal brain infection that arises in chronically immunosuppressed populations including people with HIV1 infection, patients on chronic immunosuppressive therapy such as corticosteriods for organ transplant, patients with cancer and/or autoimmune diseases (such as rheumatoid arthritis, psoriasis, and lupus erythematosis), and patients on therapies that depress the immune response (e.g., efalizumab, belatacept, rituximab, natalizumab, infliximab, among others). PML is a fatal condition caused by the lytic infection of JC polyomavirus (JCV) in the brain. However, the brain-infective form of the virus is not acquired by transmission from an infected patient. Instead, brain-infective JCV is formed by genomic rearrangement of the non-pathogenic form of the virus that resides outside of the brain in a persistently infective state within a patient. This non-pathogenic, or archetype JCV, which is detected in the kidney, genitourinary tract and bone marrow, is kept in check by the host cellular immune response. The transformation to the brain-infective form occurs when a patient undergoes a sustained disruption of cellular immunity, which could be caused by either immune-suppressing drugs to treat autoimmune disease (e.g. MS) or by development of clinical AIDS following HIV infection. In the context of immunosuppression, JCV rearranges its non-coding control region (NCCR), followed by mutations in the viral capsid protein VP1. Rearranged NCCR is thought to enable the virus to replicate in a wider range of cells, while the subsequent mutations in VP1 enable viral entry through a broader range of receptors found on the surface of cells outside the genitourinary tract. Neither the pathway to the brain nor the carrier enabling JCV to enter the brain is definitively known, but it is a slow process that takes years to complete. A characteristic marker of PML is the appearance of viral DNA in the cerebrospinal fluid (CSF). In a typical clinical case, a patient is negative for JCV DNA within 2 months of a diagnosis, after which JCV DNA is readily found in the CSF. Thus, the process of central nervous system (CNS) entry is very slow, but once virus enters the CNS, progression to disease is relatively rapid.

Lytic infection of JCV in the brain causes irreversible damage to neural tissue. Thus, it would be desirable to clear JCV from a patient early in the course of treatment. An ATKi could be used alongside therapies like Tysabri for MS, to clear JCV at the initiation of an immune-suppressing treatment.

Proof-of-concept trials related to a PML antiviral program to treat JCV infection with the marketed drug Gleevec, a well-known anticancer Abl-kinase inhibitor, were conducted. Gleevec was very useful for defining the mechanism of action, but it rapidly became clear that the human steady-state (SS) concentration of Gleevec cannot sustain an efficacious dose for an antiviral purpose (Table 1). The steady-state trough concentration, $C_{min}^{SS}$, is just 2.3-fold higher than the $EC_{50}$ of Gleevec against JCV in cell culture (Table 1). Typically, this ratio should be 4- to 9-fold above the $EC_{50}$ value for a safe and effective antiviral agent.

Improved agents for treating JCV and other infectious agents are needed.

Anti-Cancer Agents

Chronic Myeloid Leukemia (CML) is a myeloproliferative neoplasm with an incidence of 1-2 cases per 100,000 persons, and accounts for ≈15% of newly diagnosed cases of leukemia in adults. Pathogenesis of CML is linked to the fusion of the Abelson murine leukemia (ABL) gene on chromosome 9 with the breakpoint cluster region (BCR) gene on chromosome 22, resulting in expression of fusion protein, termed BCR-ABL. BCR-ABL is a constitutively active tyrosine kinase that promotes growth and replication through downstream pathways such as RAS, RAF, JUN kinase, MYC, and STAT. The consequences of BCR-ABL expression create a cytokine-independent cell cycle with aberrant apoptotic signals in response to cytokine withdrawal. The development of small molecule ATKis that potently interfere with the interaction between BCR-ABL and ATP were shown to block cellular proliferation of the malignant clone. This "targeted" approach was found to dramatically alter the natural history of the disease, improving 10-year overall survival (OS) from to ≈20% to >80%.

Three such targeted therapies have been approved for first line treatment of CML: imatinib (Gleevec®), nilotinib (Tasigna®) and dasatinib (Sprycel®). Gleevec, the first of these agents to reach market, displayed a remarkable 81% event-free survival rate and a 93% overall survival rate when CML-only related deaths were considered. But, 8-year follow-up studies revealed that only 55% of patients remained on therapy, indicating that additional options were needed to handle treatment failure and improve tolerability of Gleevec as a chronic medication. Treatment failures were often linked to the development of Gleevec resistance arising from secondary mutations in the Abl-kinase domain of the fusion protein, resulting in a loss of Gleevec potency and relapse of disease. Sprycel, a dual Abl- and SRC-kinase inhibitor, was the second approved agent and a much more potent inhibitor of BCR-ABL. Sprycel induces more rapid responses and suppression of fusion protein expression at much earlier timepoints than Gleevec. But, as a SRC inhibitor, significant side effects counterbalanced the value of the enhanced response profile that Sprycel displayed. Tasigna was developed to directly address Gleevec resistance, and, early in its development, demonstrated potent inhibitory activity against many clinically relevant BCR-ABL mutants that no longer responded to Gleevec therapy (Table 3). Like Sprycel, Tasigna was as much as 20× more potent as an inhibitor of BCR-ABL relative to Gleevec (Table 3). However, Tasigna's potency was accompanied by a side effect profile with severe adverse event frequency similar to Sprycel, limiting its utility as a chronic medication.

Thus, despite the success of targeted therapies against BCR-ABL, comorbidities and toxicities are a dominant issue in the use of these frontline ATKis for some patients. Patients at risk of developing pleural effusions, for example, such as patients with a history of lung disease (e.g., COPD), cardiac disease (e.g., congestive heart failure or pulmonary arterial hypertension) or patients with uncontrolled hypertension, make Sprycel a poor choice. Sprycel also inhibits platelet function, so patients taking anticoagulants could be at risk for bleeding complications while on Sprycel. Tasigna is associated with hyperglycemia and therefore could be detrimental if used in patients with uncontrolled diabetes. Tasigna may also prolong the QT interval and therefore may be contraindicated in patients with cardiac complications, although longer-term follow-up studies appear to be needed to confirm this observation. The non-linear accumulation of Tasigna that occurs when taken in the context of a fatty diet also places patients at risk for reaching severe dose-limiting toxicities, requiring fasting before and after dosing with Tasigna for 2 hours; as Tasigna is given 2×/day, this means patients on Tasigna are fasting as much as 8 hours out of every 24. By contrast, while Gleevec is associated with some severe AEs (e.g., leukopenia and cytopenia), its most prominent side effect is peripheral edema, which can be medically managed. Ponatinib, the most recent ATKi to reach market and which addresses nearly all Gleevec resistance, including the T315I 'gatekeeper' mutation, was subsequently found to cause a severe blood clotting syndrome and a narrowing of blood vessels after 24 months of therapy. As a result, ponatinib's utility has been severely restricted as a third-line treatment when no other options exist. Bosutinib, another recently approved Abl-SRC dual inhibitor, is considered second-line in the context of imatinib-resistance with potency that is similar to Sprycel.

Similarly, GastroIntestinal Stromal Tumors (GIST), the most common mesenchymal tumors originating in the digestive tract, have a characteristic morphology and are generally positive for CD117 (c-kit) and are primarily caused by activating mutations in the KIT or PDGFRa, both protein kinases in the Abelson-kinase family which are susceptible to treatment with ATKis. Just as found in the case of BCR-Abl associated cancers, KIT and/or PDGFRa associated GIST treated with frontline TKIs like imatinib can eventually develop resistance to therapy through the formation of secondary mutations in either KIT or PDGFRa; imatinib also displays poor response rates in KIT exon 9 and wildtype associated tumors, both of which are more responsive to higher affinity ATKis like sunitinib and regorafenib. Given the lower overall response rates of sunitinib and regorafenib relative to imatinib in front line therapy, the development of new agents with the broadest application in the manner of imatinib offers a likelihood of treatment success that will exceed the higher affinity agents like sunitinib and regorafenib.

SUMMARY OF THE INVENTION

In one aspect, the invention provides compounds represented by general formula (I) or a pharmaceutically acceptable salt thereof:

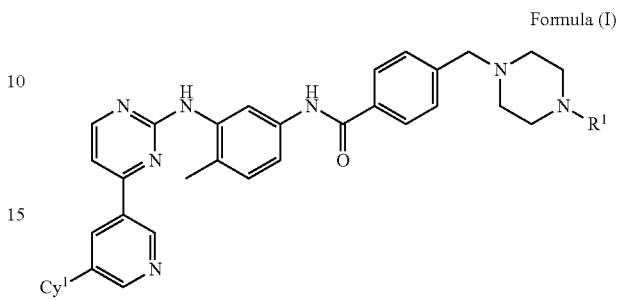

Formula (I)

wherein, independently for each occurrence,
$R^1$ is selected from hydrogen or lower alkyl; and
$Cy^1$ is selected from substituted or unsubstituted aryl, substituted or unsubstituted heteroaryl, and substituted or unsubstituted heterocyclyl, provided that $Cy^1$ is not unsubstituted pyrid-4-yl.

DETAILED DESCRIPTION OF THE INVENTION

Figure 1A:
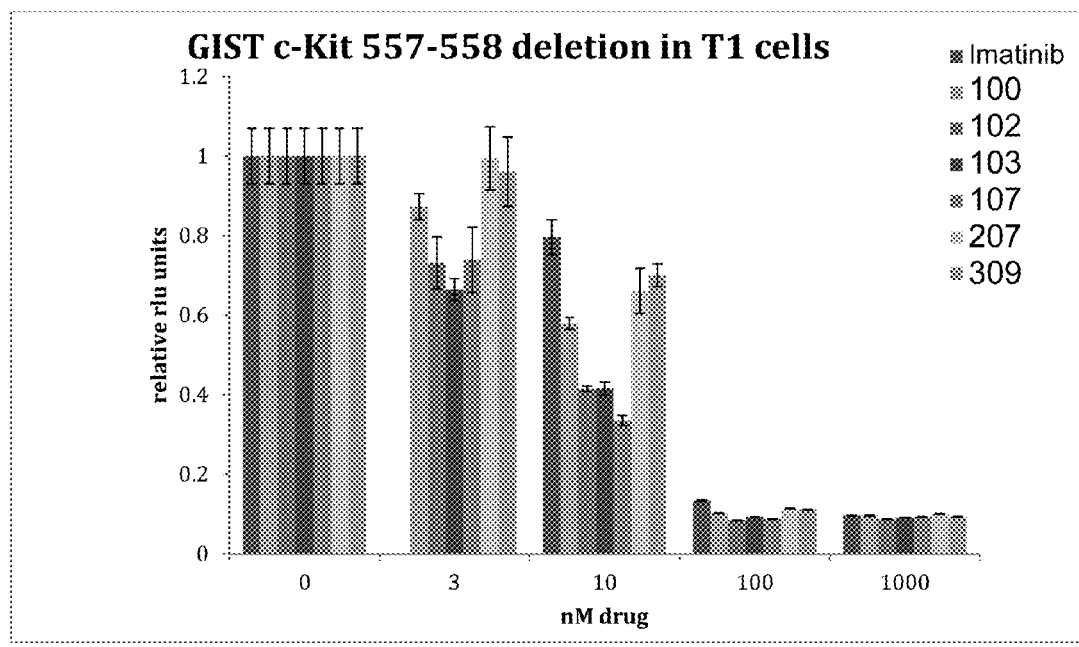
FIG. 1A shows the effect of imatinib and various compounds of the present invention on T1 cells containing the GIST-related cKit 557-558 deletion.
Figure 1B:
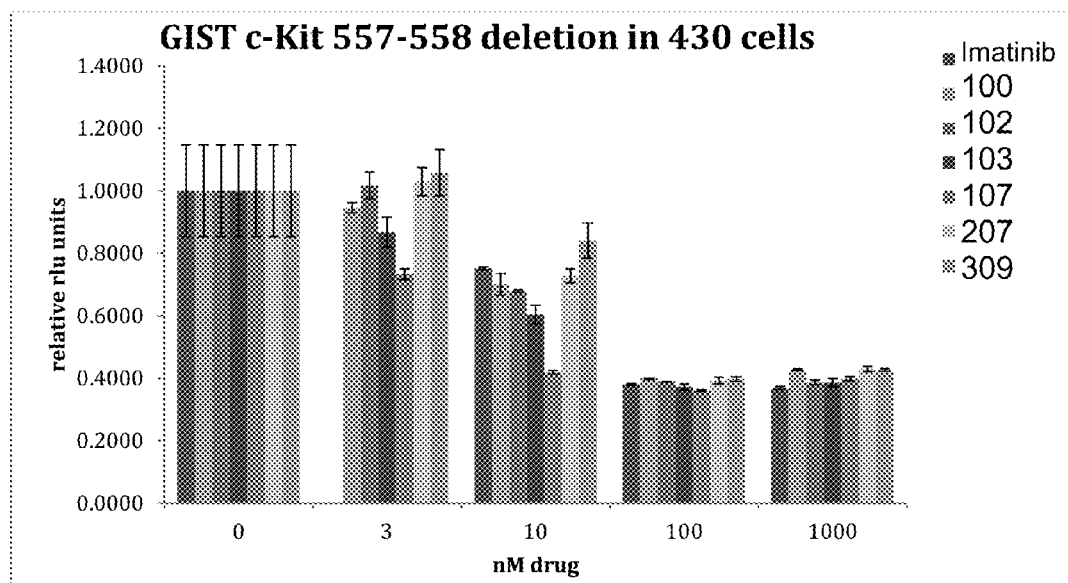
FIG. 1B shows the effect of imatinib and various compounds of the present invention on 430 cells containing the GIST-related cKit 557-558 deletion.
Figure 1C:
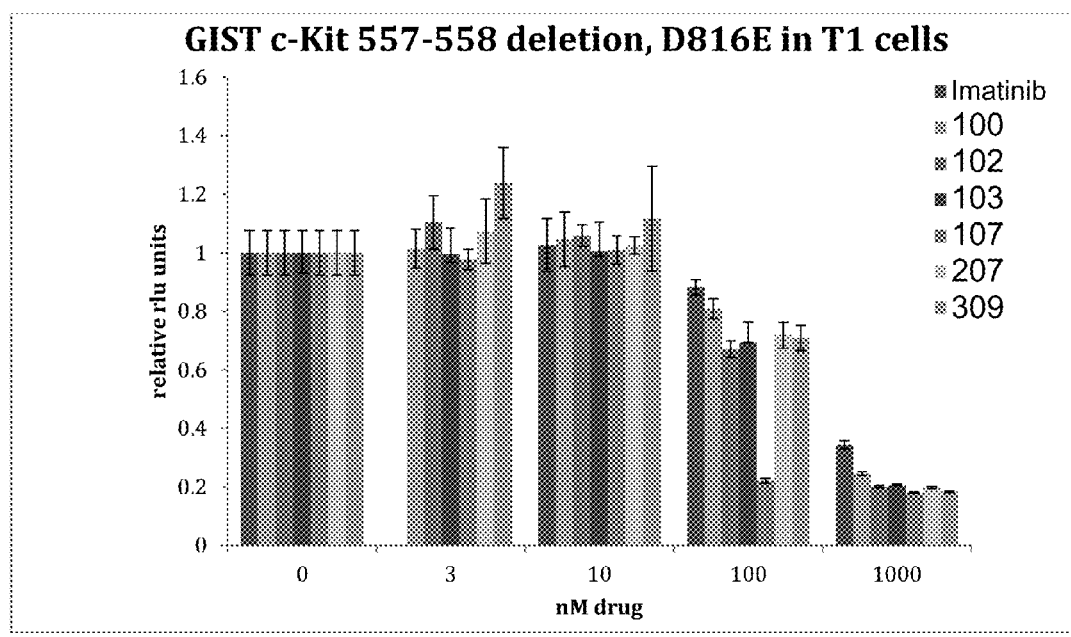
FIG. 1C shows the effect of imatinib and various compounds of the present invention on T1 cells containing the GIST-related cKit 557-558 deletion and the D816E mutation.
Figure 1D:
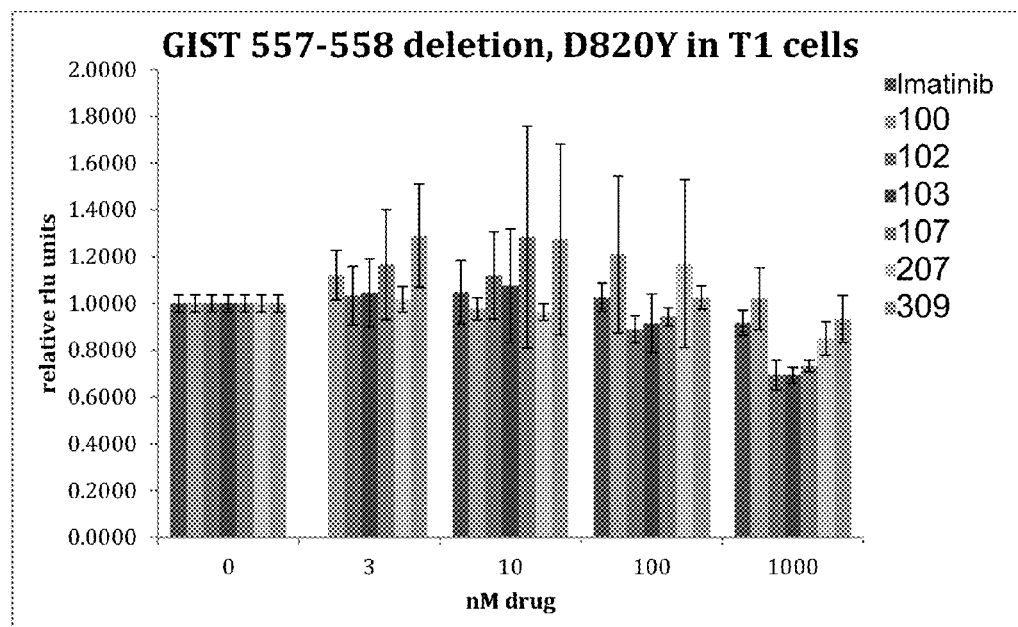
FIG. 1D shows the effect of imatinib and various compounds of the present invention on T1 cells containing the GIST-related cKit 557-558 deletion and the D820Y mutation.
Figure 1E:
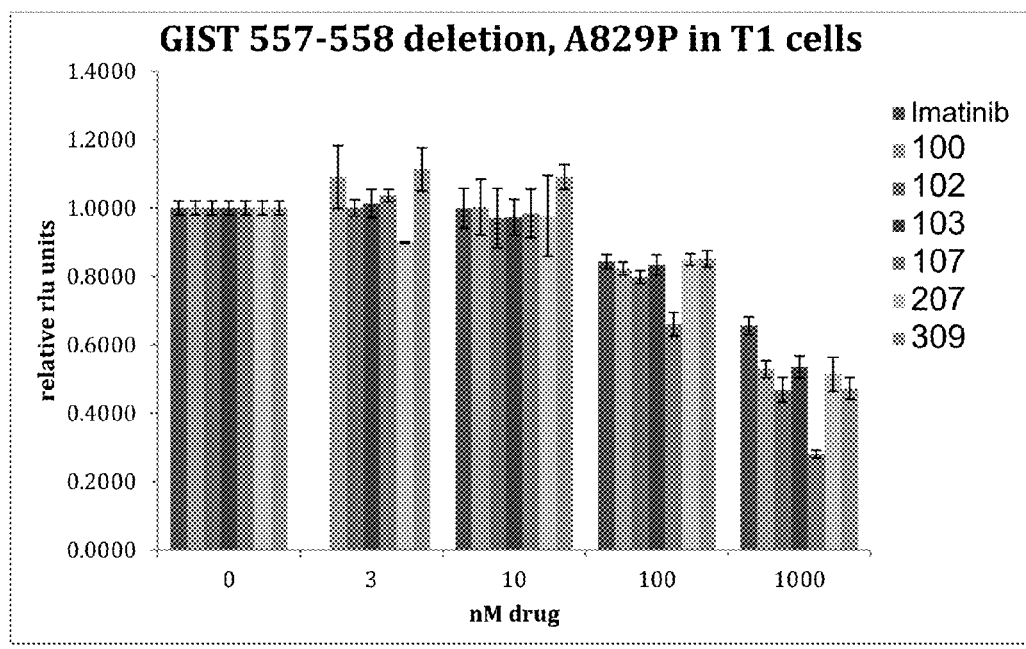
FIG. 1E shows the effect of imatinib and various compounds of the present invention on T1 cells containing the GIST-related cKit 557-558 deletion and the A829P mutation.
Figure 1F:
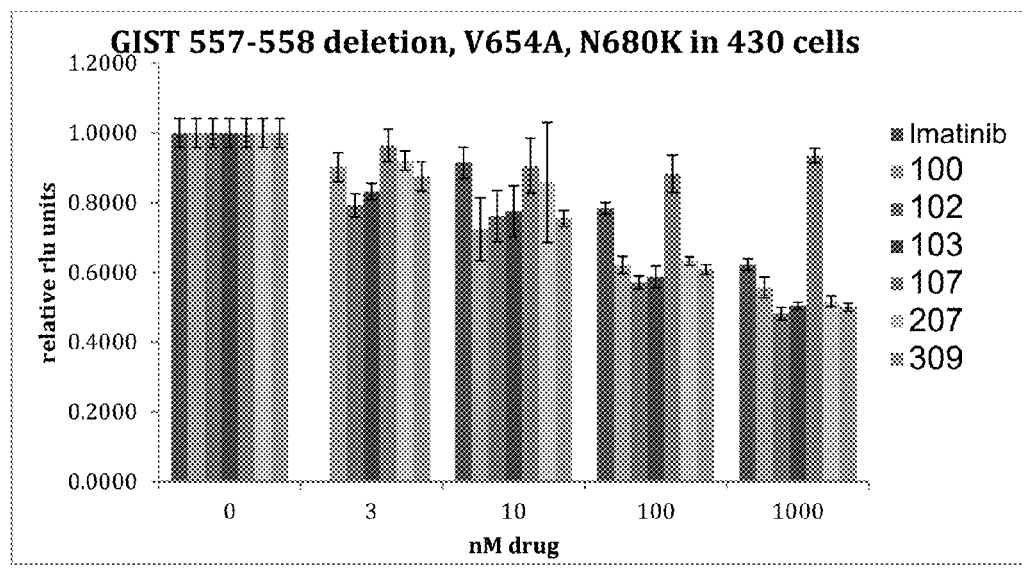
FIG. 1F shows the effect of imatinib and various compounds of the present invention on ACC-430 cells containing the GIST-related cKit 557-558 deletion and the V654A and N680K mutations.
Figure 1G:
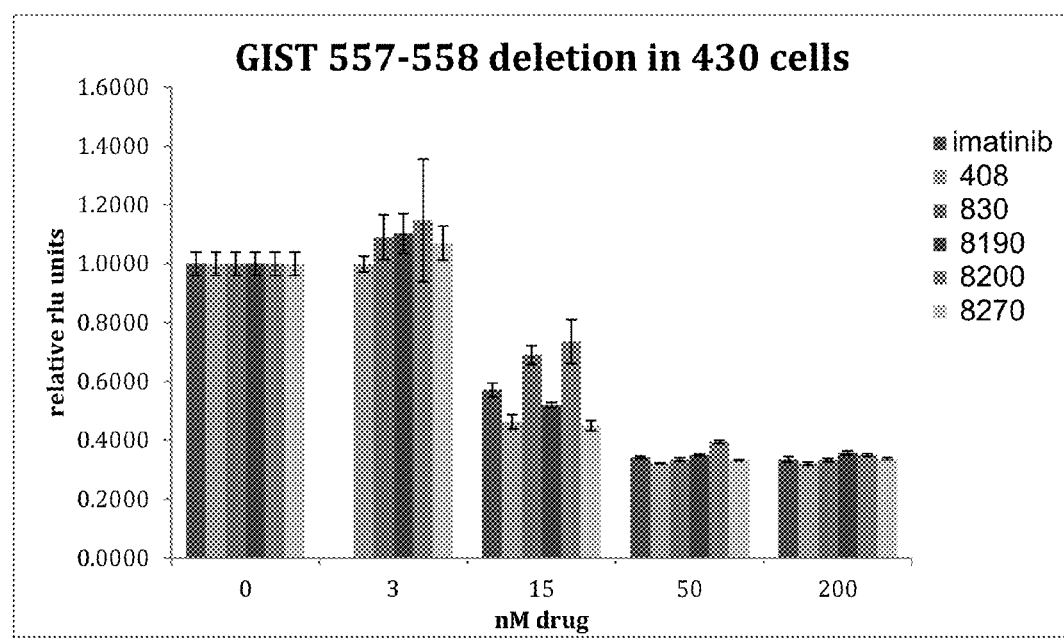
FIG. 1G shows the effect of imatinib and various compounds of the present invention on 430 cells containing the GIST-related cKit 557-558 deletion.

In one aspect, the invention provides compounds represented by formula (I) or a pharmaceutically acceptable salt thereof:

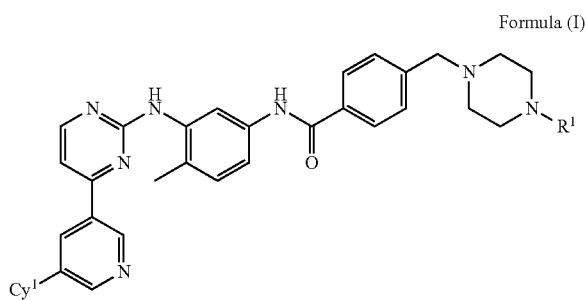

Formula (I)

wherein, independently for each occurrence,
R¹ is selected from hydrogen or lower alkyl; and
Cy¹ is selected from substituted or unsubstituted aryl, substituted or unsubstituted heteroaryl, and substituted or unsubstituted heterocyclyl,
provided that Cy¹ is not unsubstituted pyrid-4-yl.

In certain embodiments, Cy¹ is selected from:

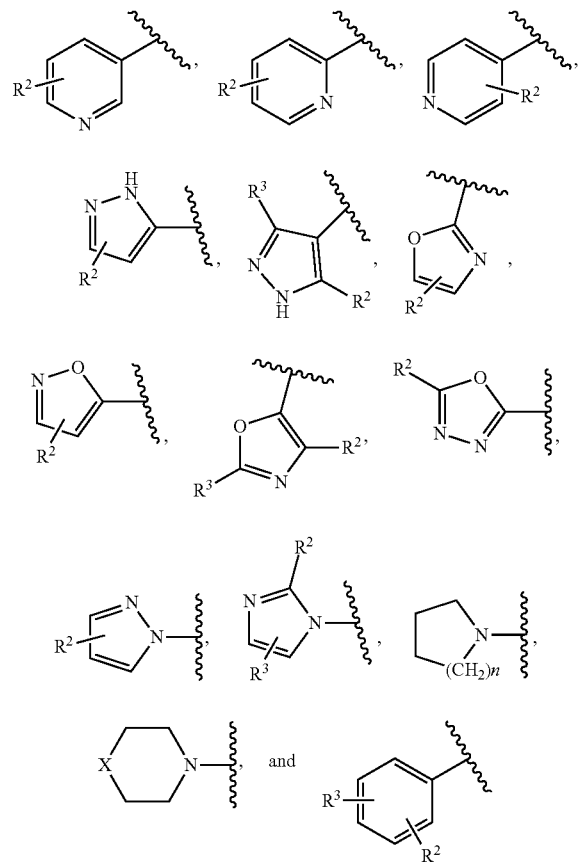

wherein, independently for each occurrence,
R² and R³ are selected from hydrogen, alkyl, amino, monoalkylamino, dialkylamino, cycloalkyl, halo, cyano, alkoxy, —C(O)OH, and —C(O)N(R⁴)(R⁴);
n is 1, 2, 3 or 4;
X is C(R⁴)₂, S, O, or NR⁴;
R⁴ is selected from hydrogen and substituted or unsubstituted alkyl, aralkyl, cycloalkyl, heterocyclyl, aryl, heteroaryl, heteroaralkyl, cycloalkylalkyl, or heterocyclylalkyl.

In certain embodiments, Cy¹ is selected from:

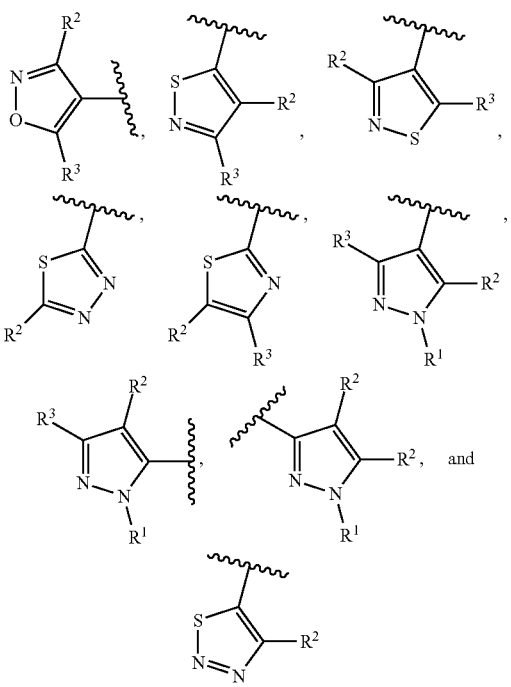

wherein, independently for each occurrence,
R¹ is selected from hydrogen or lower alkyl;
R² and R³ are selected from hydrogen, alkyl, amino, monoalkylamino, dialkylamino, cycloalkyl, halo, cyano, alkoxy, —C(O)OH, and —C(O)N(R⁴)(R⁴);
R⁴ is selected from hydrogen and substituted or unsubstituted alkyl, aralkyl, cycloalkyl, heterocyclyl, aryl, heteroaryl, heteroaralkyl, cycloalkylalkyl, or heterocyclylalkyl.

In certain other embodiments, Cy¹ is not substituted or unsubstituted pyrid-4-yl.

In certain embodiments, Cy¹ is 5-membered heteroaryl, aryl or heterocyclyl.

In certain embodiments, Cy¹ is selected from:

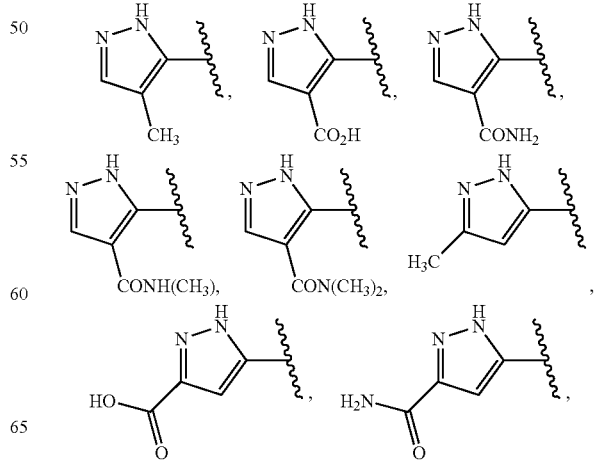

-continued

In certain embodiments, Cy¹ is selected from:

In certain embodiments, Cy¹ is selected from:

In certain embodiments, Cy¹ is selected from:

In certain preferred embodiments, R¹ is methyl, e.g., —CH₃, —CDH₂, —CD₂H, or —CD₃.

In one aspect, the invention provides a pharmaceutical composition comprising a compound as disclosed herein.

In certain embodiments, the pharmaceutical composition further comprises one or more pharmaceutically acceptable excipients.

In one aspect, the invention provides a compound or composition, as disclosed herein, for conjoint administration with one or more compounds independently selected from central nervous system drugs, such as CNS/respiratory stimulants, analgesics, narcotic agonists, narcotic antagonists, nonsteroidal anti-inflammatory/analgesic agents, behavior-modifying agents, tranquilizers/sedatives, anesthetic agents, inhalants, narcotics, reversal agents, anticonvulsants, skeletal muscle relaxants, smooth muscle relaxants, cardiovascular agents, inotropic agents, antiarrhythmic drugs, anticholinergics, vasodilating agents, agents used in treatment of shock, alpha-adrenergic blocking agents, beta-adrenergic blocking agents, respiratory drugs, bronchodilators, sympathomimetics, antihistamines, antitussives, agents for urinary incontinence/retention, urinary alkalinizers, urinary acidifiers, cholinergic stimulants, agents for urolithiasis, gastrointestinal agents, antiemetic agents, antacids, histamine H2 antagonists, gastromucosal protectants, proton pump inhibitors, appetite stimulants, GI antispasmodics-anticholinergics, GI stimulants, laxatives, saline, lubricant, surfactant, antidiarrheals, hormones/endocrine/reproductive agents, sex hormones, anabolic steroids, posterior pituitary hormones, adrenal cortical steroids, glucocorticoids, antidiabetic agents, thyroid drugs, thyroid hormones, endocrine/reproductive drugs, prostaglandins, antiinfective drugs, antiparasitics, anticoccidial agents, antibiotics, antituberculosis, aminocyclitols, cephalosporins, macrolides, penicillins, tetracyclines, lincosamides, quinolones, sulfonamides, antibacterials, antifungal agents, antiviral agents, blood modifying agents, clotting agents, anticoagulants, erythropoietic agents, antineoplastics/immunosuppressives, alkylating agents, antidotes, bone/joint agents, dermatologic agents (systemic), vitamins and minerals/nutrients, systemic acidifiers, systemic alkalinizers, anti-cancer agents, and antiviral agents.

In another aspect, the invention provides a use of a compound to treat Progressive Multifocal Leukoencephalopathy (PML), e.g., in multiple sclerosis (MS) patients on Tysabri, immunosuppressed patients (including patients with HIV1 infection), patients on chronic immunosuppressive therapy such as corticosteroids for organ transplant, patients with cancer and/or an autoimmune disease (such as rheumatoid arthritis, psoriasis, and lupus erythematosis), and patients on therapies that depress the immune response (e.g., efalizumab, belatacept, rituximab, natalizumab, infliximab, among others).

In another aspect, the invention provides a use of a compound or composition as disclosed herein for altering activity of one or more ATKs in a mammal, such as a human.

In another aspect, the invention provides a use of a compound or composition as disclosed herein for altering the function of c-Abl1 and/or c-Abl2 or any protein comprising a kinase domain of c-Abl1 and/or c-Abl2 in a mammal, such as a human.

In another aspect, the invention provides a use of a compound or composition as disclosed herein for altering the function of c-Kit or any protein comprising a kinase domain of c-Kit in a mammal, such as a human.

In another aspect, the invention provides use of a compound or composition as disclosed herein for inhibiting PGDFRa or PDGFRb or any protein comprising a kinase domain of PDGRFa or PDGRFb.

In another aspect, the invention provides use of a compound or composition as disclosed herein for treatment of cardiovascular abnormalities such as pulmonary arterial hypertension (PAH), HIV-related Kaposi's Sarcoma, Idiopathic Pulmonary Fibrosis (IPF), Diffuse Cutaneous Systemic Sclerosis or Rheumatoid Arthritis.

In another aspect, the invention provides use of a compound or composition as disclosed herein for inhibiting mutated c-Kit having one or more mutations associated with Gastrointestinal Stromal Tumor (GIST) such as those in Exon 11 (557-558 deletion), Exon 11 557-558 deletion in combination with a D186E mutation, Exon 11 557-558 deletion in combination with a D820Y mutation, Exon 11 557-558 deletion in combination with an A829P mutation, Exon 11 557-558 deletion in combination with V654K mutation, and Exon 11 557-558 deletion in combination with V654K and N680K. Mutation(s) in Exon 9 may also be accessible to ATKi treatment.

In another aspect, the invention provides a method of treating a mammal suffering from cancer, comprising administering to the mammal an effective amount of a compound or composition as disclosed herein.

In another aspect, the invention provides a method of treating Gastrointestinal Stromal Tumors (GIST), the most common mesenchymal tumors originating in the digestive tract, which have a characteristic morphology, are generally positive for CD117 (c-kit) and are primarily caused by activating mutations in the KIT or PDGFRa, both protein kinases in the Abelson-kinase family which are susceptible to treatment with ATKis, comprising administering a compound or composition, as disclosed herein, to the subject.

In another aspect, the invention provides a method for preventing or treating a bacterial infection or a viral infection in a subject, comprising administering a compound or composition, as disclosed herein, to the subject.

In certain embodiments, the invention provides for a method of preventing or treating a bacterial infection, e.g., a bacterial infection caused by *Pseudomonas aeruginosa, Chlamydia trachomatis, Escherichia coli, Helicobacter pylori, Listeria monocytogenes, Salmonella typhimurium, Shigella flexneri*, or *Mycobacterium tuberculosis*.

In certain embodiments, the invention provides for a method of preventing or treating a viral infection, e.g., a viral infection caused by a Vaccinia virus, a variola virus, a polyoma virus, a Pox virus, a Herpes virus, a cytomegalovirus (CMV), a human immunodeficiency virus, JC virus, JC polyomavirus (JCV), BK polyomavirus (BKV), Simian virus 40 (SV40), Monkeypox virus, Ebola virus, Marburg virus, Bunyavirus, Arenavirus, Alphavirus (e.g., Venezuelan equine encephalitis (VEE) or Western equine encephalitis (WEE)), Flavivirus, West Nile virus or Coronavirus (e.g., SARS).

In certain embodiments, the invention provides a method of preventing or treating a viral infection, where the viral infection is a lytic infection of JCV in the brain.

In certain embodiments, the invention provides a method of preventing or treating a bacterial or viral infection, where the subject is a human.

In another aspect, the invention provides a method of preventing or treating a bacterial or viral infection, where the compound or composition, as disclosed herein, is administered orally, nasally, buccally, sublingually, intravenously, transmucosally, rectally, topically, transdermally, subcutaneously, by inhalation, or intrathecally.

Compounds

Compounds of the invention include compounds of Formula I as disclosed above and their salts (including pharmaceutically acceptable salts). Such compounds are suitable for the compositions and methods disclosed herein.

Definitions

The term "alkyl" refers to the radical of saturated aliphatic groups, including straight-chain alkyl groups, and branched-chain alkyl groups. In preferred embodiments, a straight chain or branched chain alkyl has 30 or fewer carbon atoms in its backbone (e.g., $C_1$-$C_{30}$ for straight chains, $C_3$-$C_{30}$ for branched chains), and more preferably 20 or fewer. In certain embodiments, alkyl groups are lower alkyl groups, e.g. methyl, ethyl, n-propyl, i-propyl, n-butyl and n-pentyl.

Moreover, the term "alkyl" (or "lower alkyl") as used throughout the specification, examples, and claims is intended to include both "unsubstituted alkyls" and "substituted alkyls", the latter of which refers to alkyl moieties having substituents replacing a hydrogen on one or more carbons of the hydrocarbon backbone. In certain embodiments, a straight chain or branched chain alkyl has 30 or fewer carbon atoms in its backbone (e.g., $C_1$-$C_{30}$ for straight chains, $C_3$-$C_{30}$ for branched chains). In preferred embodiments, the chain has ten or fewer carbon ($C_1$-$C_{10}$) atoms in its backbone. In other embodiments, the chain has six or fewer carbon ($C_1$-$C_6$) atoms in its backbone.

The term "alkenyl", as used herein, refers to an aliphatic group containing at least one double bond and is intended to include both "unsubstituted alkenyls" and "substituted alkenyls", the latter of which refers to alkenyl moieties having substituents replacing a hydrogen on one or more carbons of the alkenyl group. Such substituents may occur on one or more carbons that are included or not included in one or more double bonds. Moreover, such substituents include all those contemplated for alkyl groups, as discussed below, except where stability is prohibitive. For example, substitution of alkenyl groups by one or more alkyl, carbocyclyl, aryl, heterocyclyl, or heteroaryl groups is contemplated. In preferred embodiments, a straight chain or branched chain alkenyl has 1-12 carbons in its backbone, preferably 1-8 carbons in its backbone, and more preferably 1-6 carbons in its backbone. Exemplary alkenyl groups include allyl, propenyl, butenyl, 2-methyl-2-butenyl, and the like.

The term "alkynyl", as used herein, refers to an aliphatic group containing at least one triple bond and is intended to include both "unsubstituted alkynyls" and "substituted alkynyls", the latter of which refers to alkynyl moieties having substituents replacing a hydrogen on one or more carbons of the alkynyl group. Such substituents may occur on one or more carbons that are included or not included in one or more triple bonds. Moreover, such substituents include all those contemplated for alkyl groups, as discussed above, except where stability is prohibitive. For example, substitution of alkynyl groups by one or more alkyl, carbocyclyl, aryl, heterocyclyl, or heteroaryl groups is contemplated. In preferred embodiments, an alkynyl has 1-12 carbons in its backbone, preferably 1-8 carbons in its backbone, and more preferably 1-6 carbons in its backbone. Exemplary alkynyl groups include propynyl, butynyl, 3-methylpent-1-ynyl, and the like.

The term "aralkyl", as used herein, refers to an alkyl group substituted with one or more aryl groups.

The term "aryl", as used herein, include substituted or unsubstituted single-ring aromatic groups in which each atom of the ring is carbon. Preferably the ring is a 5- to 7-membered ring, more preferably a 6-membered ring. Aryl groups include phenyl, phenol, aniline, naphthyl, biphenyl, anthracenyl and the like.

The term "cycloalkyl", as used herein, refers to the radical of a saturated aliphatic ring. In preferred embodiments, cycloalkyls have from 3-10 carbon atoms in their ring structure, and more preferably from 5-7 carbon atoms in the ring structure. Suitable cycloalkyls include cycloheptyl, cyclohexyl, cyclopentyl, cyclobutyl and cyclopropyl.

The terms "cycloalkyl" and "cycloalkenyl" refer to cyclic hydrocarbon groups of 3 to 12 carbon atoms.

The terms "halogen", "halide" and "halo", as used herein, mean halogen and include fluoro, chloro, bromo and iodo.

The terms "heterocyclyl", "heterocycle", "heterocyclo" and "heterocyclic" refer to substituted or unsubstituted non-aromatic ring structures, preferably 3- to 10-membered rings, more preferably 3- to 7-membered rings, whose ring structures include at least one heteroatom, preferably one to four heteroatoms, more preferably one or two heteroatoms. The heterocyclic group may be attached at any heteroatom or carbon atom of the ring or ring system. Exemplary monocyclic heterocyclic groups include pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridinyl, pyrazinyl, pyrimidinyl, pyridazinyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl, triazolyl, triazinyl, and the like. Exemplary bicyclic heterocyclic groups include indolyl, benzothiazolyl, benzoxazolyl, benzodioxolyl, benzothienyl, quinuclidinyl, quinolinyl, tetra-hydroisoquinolinyl, isoquinolinyl, benzimidazolyl, benzopyranyl, indolizinyl, benzofuryl, chromonyl, coumarinyl, benzopyranyl, cinnolinyl, quinoxalinyl, indazolyl, pyrrolopyridyl, furopyridinyl (such as furo [2,3-c] pyridinyl, furo [3,2-b] pyridinyl] or furo [2,3-b] pyridinyl), dihydroisoindolyl, dihydroquinazolinyl (such as 3,4-dihydro-4-oxo-quinazolinyl), tetrahydroquinolinyl and the like. Exemplary tricyclic heterocyclic groups include carbazolyl, benzindolyl, phenanthrolinyl, acridinyl, phenanthridinyl, xanthenyl and the like.

The term "heteroalkyl", as used herein, refers to a saturated or unsaturated chain of carbon atoms including at least one heteroatom (e.g., O, S, or $NR^4$, such as where $R^4$ is H or lower alkyl).

The term "heteroaryl" includes substituted or unsubstituted aromatic single ring structures, preferably 5- to 7-membered rings, more preferably 5- to 6-membered rings, whose ring structures include at least one heteroatom (e.g., O, N, or S), preferably one to four or one to 3 heteroatoms, more preferably one or two heteroatoms. When two or more heteroatoms are present in a heteroaryl ring, they may be the same or different. The term "heteroaryl" also includes polycyclic ring systems having two or more cyclic rings in which two or more carbons are common to two adjoining rings wherein at least one of the rings is heteroaromatic, e.g., the other cyclic rings can be cycloalkyls, cycloalkenyls, cycloalkynyls, aryls, heteroaryls, and/or heterocyclyls. Preferred polycyclic ring systems have two cyclic rings in which both of the rings are aromatic. Exemplary heteroaryl groups include pyrrolyl, pyrazolyl, imidazolyl, oxazolyl, isoxazolyl, thiazolyl, thiadiazolyl, isothiazolyl, furyl, thienyl, oxadiazolyl, pyridinyl, pyrazinyl, pyrimidinyl, quinolinyl, pyridazinyl, triazolyl, triazinyl, and the like.

The term "alkoxy" is intended to mean an alkyl radical, as defined herein, attached directly to an oxygen atom. Some embodiments are 1 to 5 carbons, some embodiments are 1 to 4 carbons, some embodiments are 1 to 3 carbons and some embodiments are 1 or 2 carbons. Examples include methoxy, ethoxy, n-propoxy, isopropoxy, n-butoxy, tert-butoxy, 5-isobutoxy, sec-butoxy, and the like.

The term "heteroatom", as used herein, means an atom of any element other than carbon or hydrogen. Preferred heteroatoms are nitrogen, oxygen, and sulfur.

The term "substituted" refers to moieties having substituents replacing a hydrogen on one or more carbons of the backbone. It will be understood that "substitution" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc. As used herein, the term "substituted" is contemplated to include all permissible substituents of organic compounds. In a broad aspect, the permissible substituents include acyclic and cyclic, branched and unbranched, carbocyclic and heterocyclic, aromatic and non-aromatic substituents of organic compounds. The permissible substituents can be one or more and the same or different for appropriate organic compounds. For purposes of the invention, the heteroatoms such as nitrogen may have hydrogen substituents and/or any permissible substituents of organic compounds described herein which satisfy the valences of the heteroatoms. Substituents can include any substituents described herein, for example, a halogen, a hydroxyl, a carbonyl (such as a carboxyl, an alkoxycarbonyl, a formyl, or an acyl), a thiocarbonyl (such as a thioester, a thioacetate, or a thioformate), an alkoxyl, an alkylthio, an acyloxy, a phosphoryl, a phosphate, a phosphonate, an amino, an amido, an amidine, an imine, a cyano, a nitro, an azido, a sulfhydryl, an alkylthio, a sulfate, a sulfonate, a sulfamoyl, a sulfonamido, a sulfonyl, a heterocyclyl, an aralkyl, or an aromatic or heteroaromatic moiety.

Unless specifically stated as "unsubstituted," references to chemical moieties herein are understood to include substituted variants. For example, reference to an "aryl" group or moiety implicitly includes both substituted and unsubstituted variants.

The term "unsaturated ring" includes partially unsaturated and aromatic rings.

As used herein, the term "tumoral disease" refers to a hyperproliferative disease, such as cancer.

As used herein, the term "conjoint administration" means administration of two or more agents to a subject of interest as part of a single therapeutic regimen. The administration(s) can be either simultaneous or sequential, i.e., administering one agent followed by administering of a second (and/or a third one, etc.) at a later time, as long as the agents administered co-exist in the subject being treated, or at least one agent will have the opportunity to act upon the same target tissues of other agents while said target tissues are still under the influence of said other agents. In a certain embodiment, agents to be administered can be included in a single pharmaceutical composition and administered together. In a certain embodiment, the agents are administered simultaneously, including through separate routes. In a certain embodiment, one or more agents are administered continuously, while other agents are administered only at predetermined intervals (such as a single large dosage, or twice a week at smaller dosages, etc.).

The present invention includes within its scope the salts and isomers. Compounds of the present invention may in some cases form salts, which are also within the scope of this invention. The term "salt(s)", as employed herein, denotes acidic and/or basic salts formed with inorganic and/or organic acids and bases. Zwitterions (internal or inner salts) are included within the term "salt(s)" as used herein (and may be formed, for example, where the R substituents comprise an acid moiety such as a carboxyl group). Also included herein are quaternary ammonium salts such as alkylammonium salts. Pharmaceutically acceptable (i.e., non-toxic, physiologically acceptable) salts are preferred, although other salts are useful, for example, in isolation or purification steps which may be employed during preparation. Salts of the compounds may be formed, for example, by reacting a compound with an amount of acid or base, such as an equivalent amount, in a medium such as one in which the salt precipitates or in an aqueous medium followed by lyophilization.

Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecyl sulfates, ethanesulfonates, fumarates, glucoheptanoates, glycerophosphates, hemisulfates, heptanoates, hexanoates, hydrochlorides, hydrobromides, hydroiodides, 2-hydroxy ethanesulfonates, lactates, maleates, methanesulfonates, 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates, undecanoates, and the like.

Exemplary basic salts (formed, for example, wherein the substituent comprise an acidic moiety such as a carboxyl group) include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines, N-methyl-D-glucamines, N-methyl-D-glucamides, t-butyl amines, and salts with amino acids such as arginine, lysine and the like. The basic nitrogen-containing groups may be quaternized with agents such as lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), aralkyl halides (e.g., benzyl and phenethyl bromides), and others.

Solvates of the compounds of the invention are also contemplated herein. Solvates of the compounds of formula I are preferably hydrates or other pharmaceutically acceptable solvates.

All stereoisomers of the present compounds, such as those which may exist due to asymmetric carbons on the R substituents of the compound, including enantiomeric and diastereomeric forms, are contemplated within the scope of this invention. Individual stereoisomers of the compounds of the invention may, for example, be substantially free of other isomers, or may be admixed, for example, as racemates or with all other, or other selected, stereoisomers. The chiral centers of the present invention may have the S or R configuration.

As used herein, the term "treating" or "treatment" includes reversing, reducing, or arresting the symptoms, clinical signs, and underlying pathology of a condition in manner to improve or stabilize a subject's condition. As used herein, and as well understood in the art, "treatment" is an approach for obtaining beneficial or desired results, including clinical results. Beneficial or desired clinical results can include, but are not limited to, alleviation or amelioration of one or more symptoms or conditions, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment.

As used herein, a therapeutic that "prevents" a disorder or condition refers to a compound that, in a statistical sample, reduces the occurrence of the disorder or condition in the treated sample relative to an untreated control sample, or delays the onset or reduces the severity of one or more symptoms of the disorder or condition relative to the untreated control sample.

The present application also envisages within its scope the effect of selection of suitable counterions. The counterion of the compounds of the present invention may be chosen by selecting the dissociation constant for the drug capable of ionization within the said pH range. By estimating the ionized and un-ionized drug concentration of any compound (using well established equations such a Henderson-Hasselbach equation), the solubility and consequently the absorption of the drug may be altered.

The compounds generated may be present as a single stereoisomer (e.g., enriched to at least 95% purity relative to the total amount of all stereoisomers present), a racemate, or a mixture of enantiomers or diastereomers in any ratio.

Pharmaceutical Compositions

The present invention further provides pharmaceutical compositions comprising a compound of formula (I) or its pharmaceutically acceptable salt thereof as an active ingredient along with pharmaceutically acceptable additives/excipients/adjuvants/vehicles.

Compounds of the present invention may be used in a pharmaceutical composition, e.g., combined with a pharmaceutically acceptable carrier, for administration to a patient. Such a composition may also contain diluents, fillers, salts, buffers, stabilizers, solubilizers, and other materials well known in the art. The term "pharmaceutically acceptable" means a non-toxic material that does not interfere with the effectiveness of the biological activity of the active ingredient(s). The characteristics of the carrier will depend on the route of administration. Such additional factors and/or agents may be included in the pharmaceutical composition to produce a synergistic effect with compounds of the invention, or to minimize side effects caused by the compound of the invention.

The pharmaceutical compositions of the invention may be in the form of a liposome or micelles in which compounds of the present invention are combined, in addition to other pharmaceutically acceptable carriers, with amphipathic agents such as lipids which exist in aggregated form as micelles, insoluble monolayers, liquid crystals, or lamellar layers in aqueous solution. Suitable lipids for liposomal formulation include, without limitation, monoglycerides, diglycerides, sulfatides, lysolecithin, phospholipids, saponin, bile acids, and the like. Preparation of such liposomal formulations is within the level of skill in the art, as disclosed, for example, in U.S. Pat. Nos. 4,235,871; 4,501,728; 4,837,028; and 4,737,323, all of which are incorporated herein by reference.

The composition may be administered in a variety of ways including orally, nasally, buccally, sublingually, intravenously, transmucosally, parenterally, by inhalation, spray, transdermally, subcutaneously, intrathecally, topically or rectally and may be formulated according to methods known in the art.

The effective dosage form for a mammal may be about 0.1-100 mg/kg of body weight of active compound, which may be administered as a single dose or in the form of individual doses, such as from 1 to 4 times a day.

The mammal may be an adult human.

The compounds of the present invention may optionally be administered with one or more additional agents. Exemplary additional agents include one or more compounds independently selected from central nervous system drugs, such as CNS/respiratory stimulants, analgesics, narcotic agonists, narcotic antagonists, nonsteroidal anti-inflammatory/analgesic agents, behavior-modifying agents, tranquilizers/sedatives, anesthetic agents, inhalants, narcotics, reversal agents, anticonvulsants, skeletal muscle relaxants, smooth muscle relaxants, cardiovascular agents, inotropic agents, antiarrhythmic drugs, anticholinergics, vasodilating agents, agents used in treatment of shock, alpha-adrenergic blocking agents, beta-adrenergic blocking agents, respiratory drugs, bronchodilators, sympathomimetics, antihistamines, antitussives, agents for urinary incontinence/retention, urinary alkalinizers, urinary acidifiers, cholinergic stimulants, agents for urolithiasis, gastrointestinal (GI) agents, antiemetic agents, antacids, histamine H2 antagonists, gastromucosal protectants, proton pump inhibitors, appetite stimulants, GI antispasmodics-anticholinergics, GI stimulants, laxatives, saline, bulk producing, lubricant, surfactant, antidiarrheals, hormones/endocrine/reproductive agents, sex hormones, anabolic steroids, posterior pituitary hormones, adrenal cortical steroids, glucocorticoids, antidiabetic agents, thyroid drugs, thyroid hormones, misc. endocrine/reproductive drugs, prostaglandins, antiinfective drugs, antiparasitics, anticoccidial agents, antibiotics, antituberculosis, aminocyclitols, cephalosporins, macrolides, penicillins, tetracyclines, lincosamides, quinolones, sulfonamides, antibacterials, antifungal agents, antiviral agents, blood modifying agents, clotting agents, anticoagulants, erythropoietic agents, antineoplastics/immunosuppressives, alkylating agents, antidotes, bone/joint agents, dermatologic agents (systemic), vitamins and minerals/nutrients, systemic acidifiers, systemic alkalinizers, anti-cancer agents, and antiviral agents.

A. Methods of Use

The present invention further provides a method of prophylaxis and/or treatment of, and/or ameliorating the symptoms of, diseases, comprising administering a therapeutically effective amount of a compound of formula (I) or pharmaceutically acceptable salts thereof or pharmaceutical compositions comprising the compound of formula (I) as the active ingredient.

The compounds of the present invention are useful as c-ABL1 and/or c-ABL2 inhibitors and are useful in all disorders where alteration of the amount of c-ABL1 and/or c-ABL2 is required in mammals, including humans. The compounds of the present invention may also act as PGDFRa and PGDFRb inhibitors in mammals, including humans. PDGFRa/b is associated with both cancer (e.g. GIST) as well as cardiovascular abnormalities such as pulmonary arterial hypertension (PAH). The compounds of the present invention may also act as inhibitors of stem cell factor receptor (SCFR), also known as c-Kit and mutations in c-Kit, in mammals, including humans. The compounds of the present invention also inhibit LCK, and thus may be useful in treating chronic lymphocytic leukemia (CLL).

The compounds of the present invention may be used to treat mammals, including humans, suffering from a tumoral disease a compound of formula (I), e.g., in a therapeutically effective amount.

Imatinib mesylate (Gleevec) has been shown to be effective against poxvirus infections by disabling host proteins essential to the virus life cycle (Nature Medicine, 2005, vol. 11, 7, page 731-739) and without interfering with the acquisition of immune memory (Journal of Virology, 2011, vol. 85, 1, p. 21-31).

Similarly, by targeting the host gene products rather the virus itself, administration of imatinib mesylate or nilotinib may be useful in treating Ebola and Marburg virus infections (Science Translational Medicine, 2012, vol. 4, 123, page 1-10; Antiviral Research, 2014, vol. 106, pages 86-94). Furthermore, Abl family kinases have been shown to regulate the susceptibility of cells to polyomavirus infection by modulating gangliosides required for viral attachment (Journal of Virology, 2010, vol. 84, 9, p. 4243-4251). Hence, Abl kinase inhibitor, e.g., a compound of formula (I), may prove useful to treat or prevent a polyomavirus infection.

The present application provides a method for preventing or treating a bacterial infection or a viral infection in a subject using a compound of formula (I) as described herein. In certain embodiments, the bacterial infection is caused by *Pseudomonas aeruginosa, Chlamydia trachomatis, Escheri-* chia coli, *Helicobacter pylori, Listeria monocytogenes, Salmonella typhimurium, Shigella flexneri,* or *Mycobacterium tuberculosis.*

In certain embodiments, *Mycobacterium tuberculosis* causes MDR-tuberculosis or XDR-tuberculosis.

In certain embodiments, the viral infection is caused by a Vaccinia virus, a variola virus, a polyoma virus, a Pox virus, a Herpes virus, a cytomegalovirus (CMV), a human immunodeficiency virus, JC virus, JC polyomavirus (JCV), BK virus, Simian virus 40 (SV40), Monkeypox virus, Ebola virus, Marburg virus, Bunyavirus, Arenavirus, Alphavirus (e.g., Venezuelan equine encephalitis (VEE), Western equine encephalitis (WEE)), Flavivirus, West Nile virus or Coronavirus (e.g., SARS).

In some embodiments, the compounds described in the present application have improved/maintain desirable safety and toxicity profile relative to imatinib mesylate.

In some embodiments, the compounds described in the present application are more soluble than imatinib mesylate in saline and/or at biologically useful pH ranges.

EXEMPLIFICATION

Example 1: Synthetic Protocols

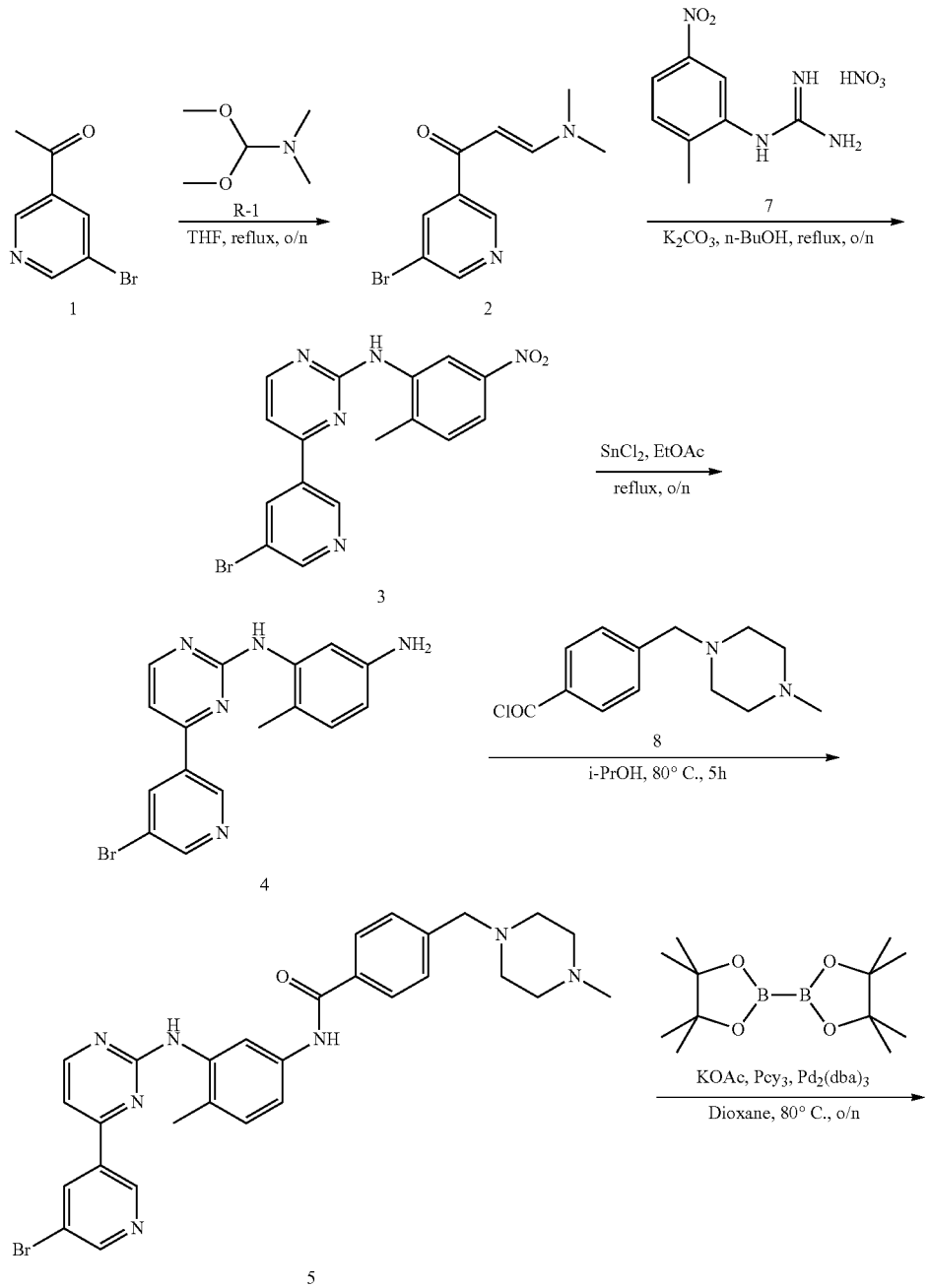

Scheme 1: Synthesis of Intermediates 5 and 6

-continued

Synthesis of (E)-1-(5-bromopyridin-3-yl)-3-(dimethylamino)prop-2-en-1-one (2)

A solution of 1 (40.0 g, 200 mmol) and R-1 (119.0 g, 1000 mmol) in 500 mL of THF was stirred at 70° C. overnight. TLC indicated the reaction was completed. The mixture was cooled to room temperature and removed the solvent at reduced pressure. The resulting solid was washed with hexane to afford 2 as a yellow solid (47.2 g, 93%).

Synthesis of 4-(5-bromopyridin-3-yl)-N-(2-methyl-5-nitrophenyl)pyrimidin-2-amine (3)

A mixture of 2 (45 g, 176.5 mmol), 7 (40.6 g, 159.2 mmol), $K_2CO_3$ (44.0 g, 318.8 mmol) in 500 mL of n-BuOH was heated at 120° C. for 16 hours. The reaction mixture was filtered, and the solvent was removed at reduced pressure. The residue was purified by chromatography column (silica gel, eluted with petroleum ether (PE)/ethyl acetate (EA), PE/EA=2:1) to afford 3 (47.0 g, 70%) was a light yellow solid.

Synthesis of $N^1$-(4-(5-bromopyridin-3-yl)pyrimidin-2-yl)-6-methylbenzene-1,3-diamine (4)

A solution of 3 (45.0 g, 116.9 mmol) and $SnCl_2$ (132.0 g, 585 mmol) in 300 mL of EtOAc was heated to reflux overnight, then the reaction was cooled to room temperature, filtered and the solution was concentrated at reduced pressure to afford 4 (44.0 g, 100%). It was directly used for the next step without any further purification.

Synthesis of N-(3-(4-(5-bromopyridin-3-yl)pyrimidin-2-ylamino)-4-methylphenyl)-4-((4-methylpiperazin-1-yl)methyl)benzamide (5)

The above crude 4 (30.0 g, 84.5 mmol) and 8 (40.0 g, 123.0 mmol) were dissolved in 300 mL of i-BuOH, then the resulting solution was warmed to 80° C. for about 5 hours, after completion of the reaction, the mixture was cooled to room temperature, and removed the solvent under reduced pressure. The resulting residue was purified by flash chromatography on silica gel (Hexane/EA=2:1) to afford 5 (45.0 g, 93%) as a yellow solid.

Synthesis of 5-(2-(2-methyl-5-(4-((4-methylpiperazin-1-yl)methyl)benzamido)phenylamino)pyrimidin-4-yl)pyridin-3-ylboronic acid (6)

A mixture of 5 (10.0 g, 17.5 mmol), KOAc (2.8 g, 28.1 mmol), $PCy_3$ (0.3 g, 1.1 mmol), $Pd_2(dba)_3$ (0.4 g, 0.5 mmol) and 4,4,4',4',5,5,5',5'-octamethyl-2,2'-bi(1,3,2-dioxaborolane) (7.1 g, 28.0 mmol) in dioxane (150 mL), was stirred at 80° C. overnight, after completion of the reaction. The reaction solution was removed at reduced pressure to afford crude 6 (11.0 g, yield 100%) as yellow solid. It was directly used for next step without further purification.

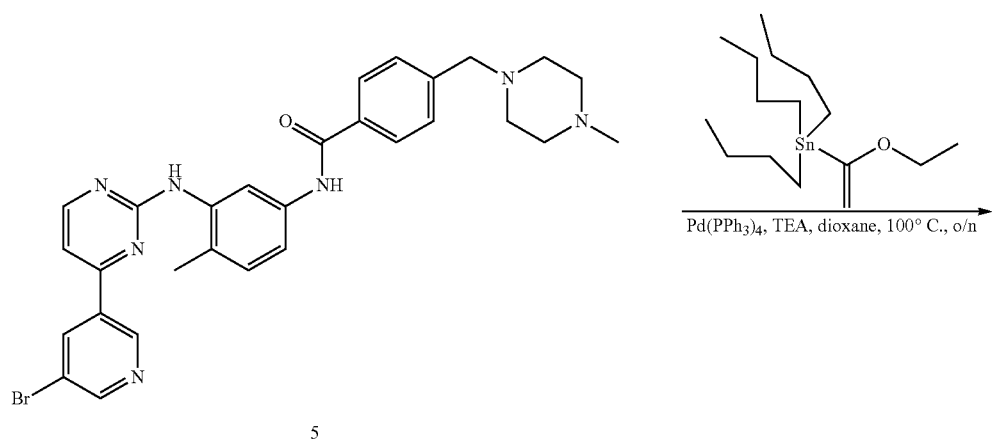
5
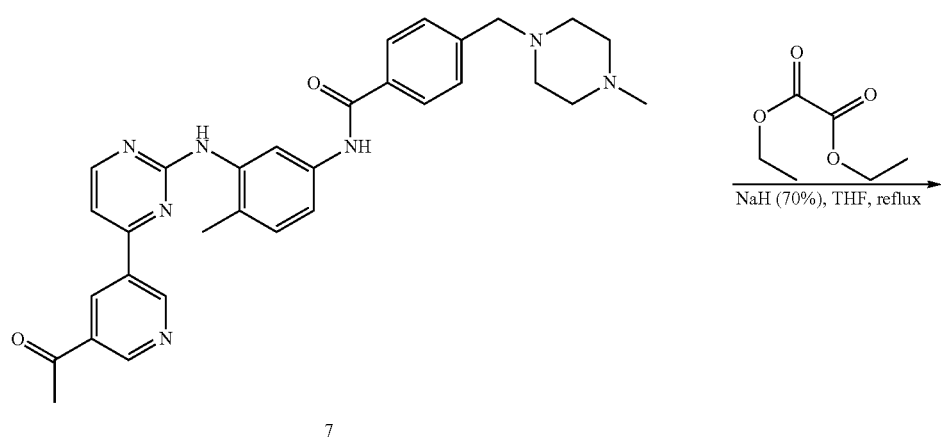
7
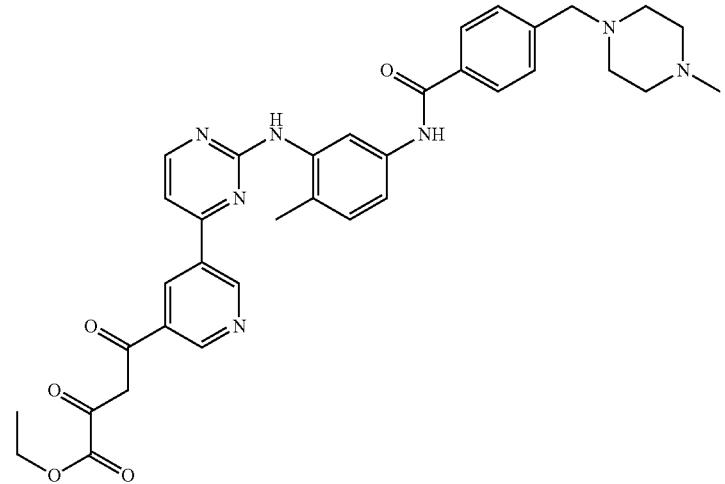
8

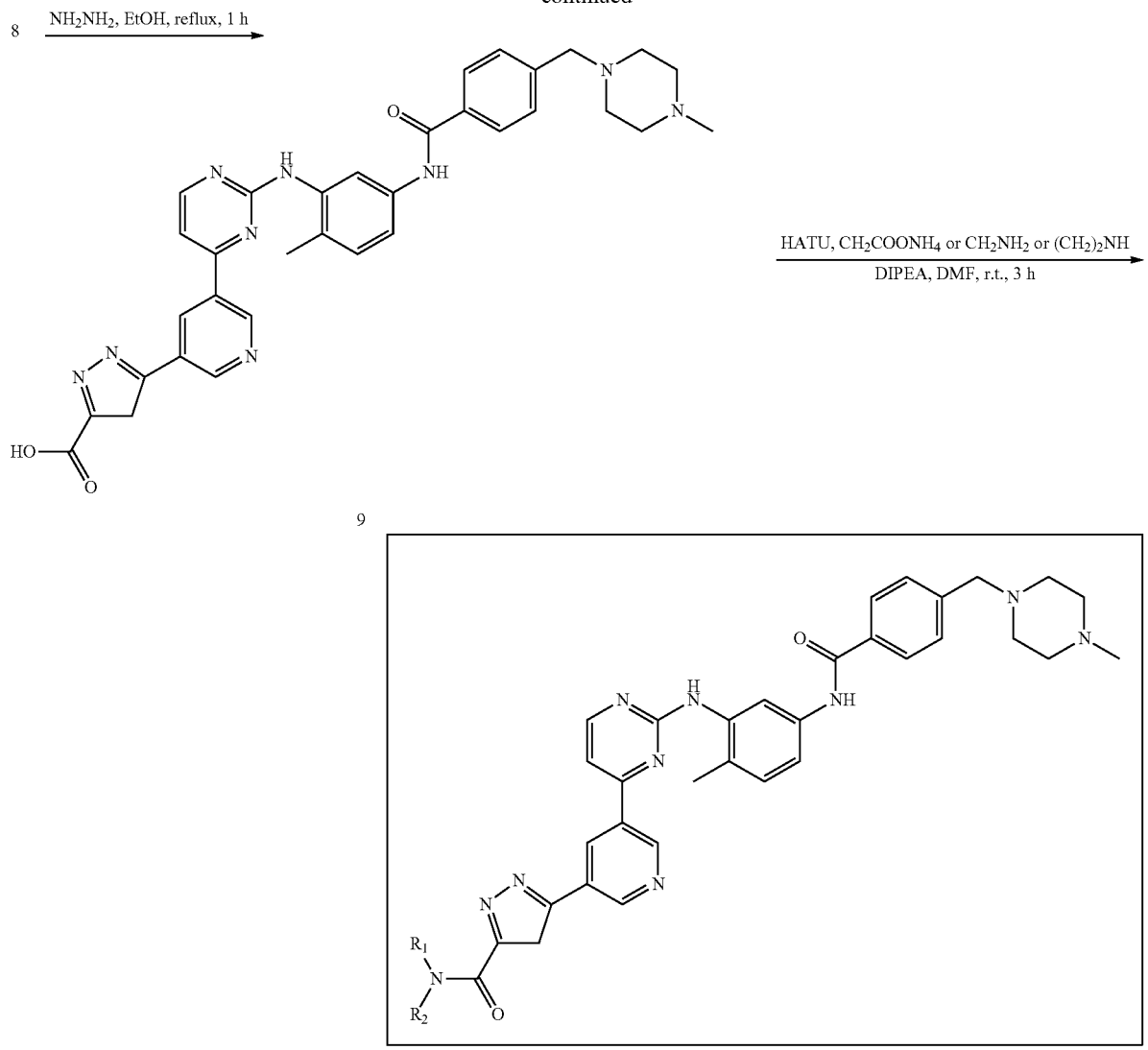

Synthesis of N-(3-(4-(5-acetylpyridin-3-yl)pyrimidin-2-ylamino)-4-methylphenyl)-4-((4-methylpiperazin-1-yl)methyl)benzamide (7)

A solution of 5 (1.1 g, 2.0 mmol), tributyl(1-ethoxyvinyl) stannane (0.9 g, 2.6 mmol), Pd(PPh$_3$)$_4$(0.2 g, 0.1 mmol) and triethylamine (0.3 g, 3.0 mmol) in degassed dioxane (50 mL) was heated to reflux for 24 hours. The solvent was then evaporated in vacuo and the residue was filtered through a thick pad of SiO$_2$. The solid obtained was taken up in dry THF (60 ml), cooled to 0° C., and treated with 1N HCl. The solution was stirred for 2 hours at room temperature and then neutralized with sat. aq. NaHCO$_3$. The mixture was extracted with EA and the organic layers were washed with brine, dried over Na$_2$SO$_4$, and concentrated in vacuo. The residue was purified by flash chromatography (silica gel, eluted with PE/EA=2:1) to afford 7 (1.0 g, 94%) as a white solid.

Synthesis of ethyl 4-(5-(2-(2-methyl-5-(4-((4-methylpiperazin-1-yl)methyl)benzamido)phenylamino)pyrimidin-4-yl)pyridin-3-yl)-2,4-dioxobutanoate (8)

Diethyl oxalate (0.4 g, 2.3 mmol) was added to a suspension of sodium hydride (70 percent, 0.2 g) in 15 mL of tetrahydrofuran, and refluxed for about 15 min. Then a solution of 7 (1.0 g, 1.9 mmol) in 5 mL of tetrahydrofuran was added dropwise over 30 min, and refluxed for 90 min. After cooling down, the reaction mixture was poured into ice-cold water, which was neutralized with diluted hydrochloric acid and extracted with ethyl acetate, dried over Na$_2$SO$_4$, and concentrated. The crude product 8 (0.8 g, 67%) was used for the next step without any further purification.

Synthesis of 5-(5-(2-(2-methyl-5-(4-((4-methylpiperazin-1-yl)methyl)benzamido)phenylamino)pyrimidin-4-yl)pyridin-3-yl)-4H-pyrazole-3-carboxylic acid (9)

To a solution of 8 (0.8 g, 1.26 mmol) in 20 mL of EtOH, hydrazine (0.1 g, 2.54 mmol) was added. The resulting mixture was heated to reflux for 60 min. The solution was removed under reduced pressure, and the residue was purified by prep-HPLC (basic) to afford 9 (0.6 g, 78%) as a white solid.
Synthesis of Library Compounds
R =
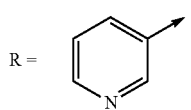
101
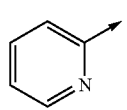
102
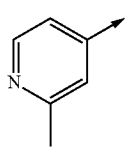
103
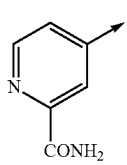
104
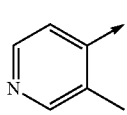
105
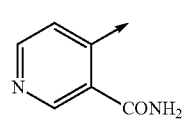
106
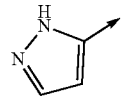
107
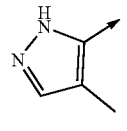
108
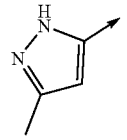
113
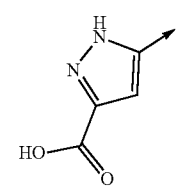
114
-continued
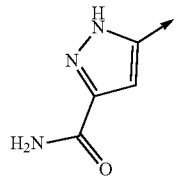
115
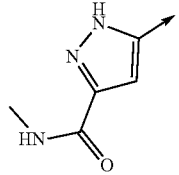
116
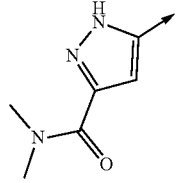
117
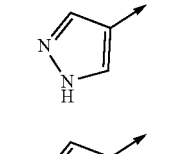
118
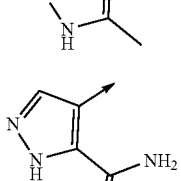
119
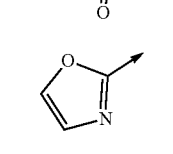
200
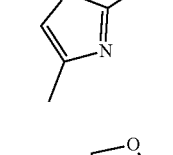
201
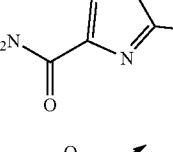
202
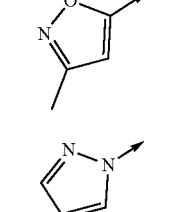
203
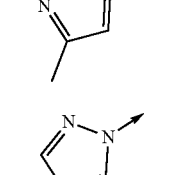
207
303

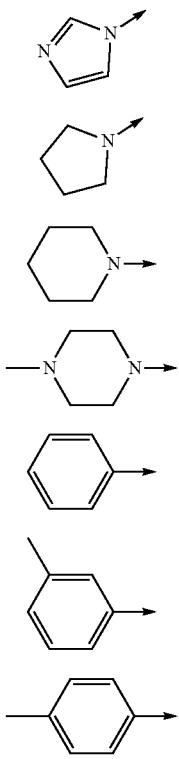
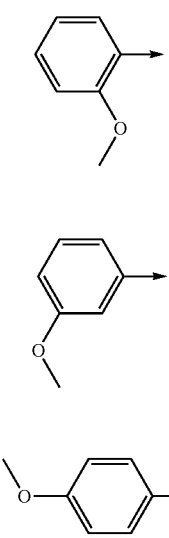
General Procedure:
A solution of 9 (160 mg, 0.26 mmol), HATU (148 mg, 0.39 mmol), R₁R₂NH (1.2 e.q.) and DIPEA (70 mg, 0.54 mmol) in 2 mL of DMF was stirred for 3 hours at room temperature. The resulting mixture was evaporated under reduced pressure and the residue was purified by prep-HPLC to afford desired library compounds.
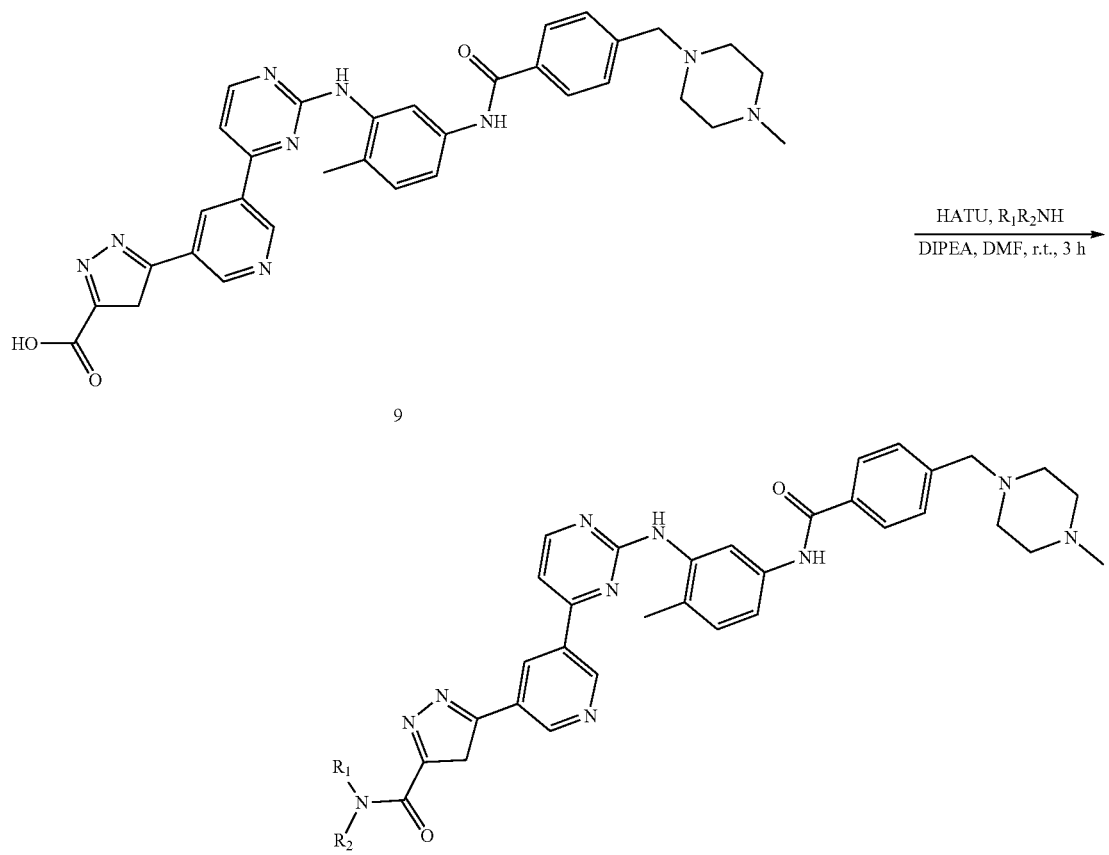

Compounds 115, 116 and 117 were prepared using this general procedure.

General Procedure:

A mixture of 5 (200 mg, 0.35 mmol), RB(OH)$_2$ (2.0 eq.), Pd(PPh$_3$)$_4$ (40 mg, 0.03 mmol), Na$_2$CO$_3$ (112 mg, 1.05 mmol) in dioxane (4 mL) and water (1 mL), The resulting reaction mixture was irradiated for 90 min in a microwave oven. Then the reaction mixture was cooled to room temperature and concentrated at reduced pressure. The residue was purified by prep-HPLC to afford desired library compounds as a solid.

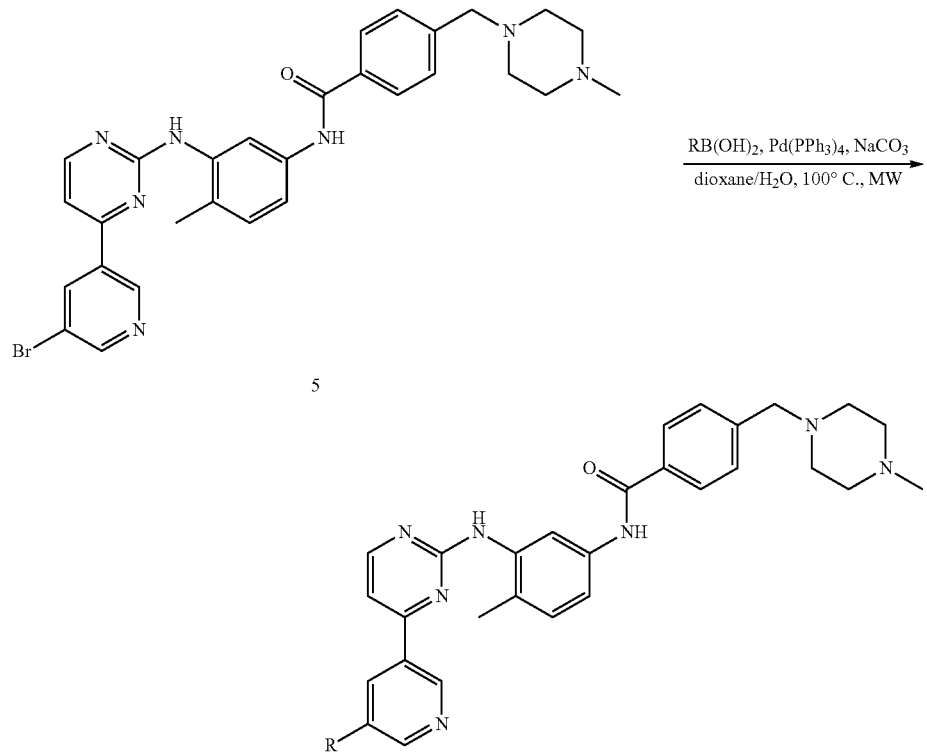

Compounds 101, 102, 103, 118, 201, 202, 309, 401, 402, 403, 404 and 405 were prepared using this general procedure.

General Procedure:

A mixture of 6 (150 mg, 0.34 mmol), RBr or RI (2.0 eq.), Pd(dppf)Cl$_2$ (57 mg, 0.07 mmol), Cs$_2$CO$_3$ (280 mg, 0.85 mmol) in i-PrOH (4 mL) and water (1 mL) was irradiated for 30 min in a microwave oven. Then the reaction solution was cooled to room temperature and concentrated at reduced pressure. The residue was purified by prep-HPLC to give desired library compounds as a solid.

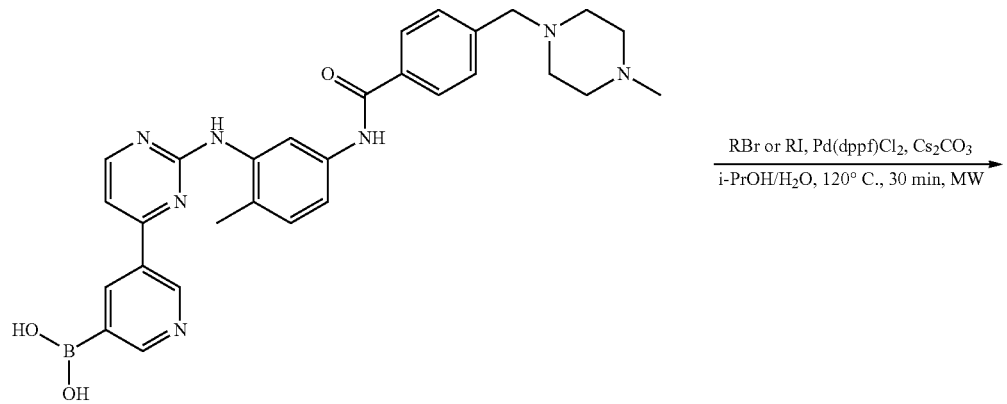

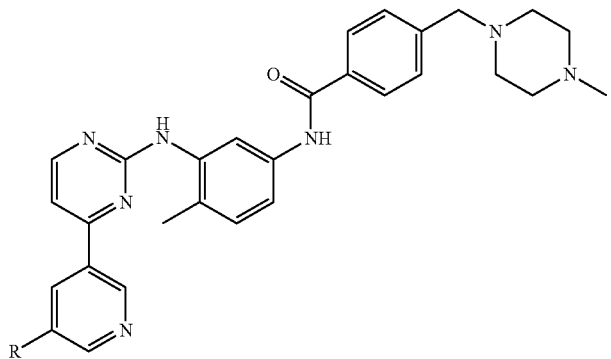

Compounds 104, 105, 106, 108, 113, 119, 203 were prepared using this general procedure.

General Procedure:

A solution of 5 (200 mg, 0.35 mmol), R-305, R-306, or R308 (3.0 eq.), Pd$_2$(dba)$_3$ (25 mg, 0.03 mmol), t-BuOK (157 mg, 1.40 mmol), BINAP (22 mg, 0.03 mmol) in 5 mL of NMP was irradiated for 90 min at 150° C. in a microwave oven. Then the reaction solution was cooled to room temperature and concentrated at reduced pressure. The residue was purified by prep-HPLC to desired compounds as a solid.

Compounds 305, 306, 308 were prepared using this general procedure.

General Procedures: To a solution of 5 (200 mg, 0.35 mmol), K$_3$PO$_4$ (149 mg, 0.70 mmol), DMCDA (7 mg, 0.05 mmol) and CuI (10 mg, 0.05 mmol) in 2 mL of DMF was added R-303 or R-304 (2.0 e.q). The resulting mixture was stirred at 120° C. overnight. The reaction mixture was cooled to room temperature, and water (0.5 mL) was added and extracted with EA (3 mL*3). The combined organic layers were dried over Na$_2$SO$_4$ and concentrated in vacuo. And the residue was purified by prep-HPLC to afford desired library compounds as a solid.

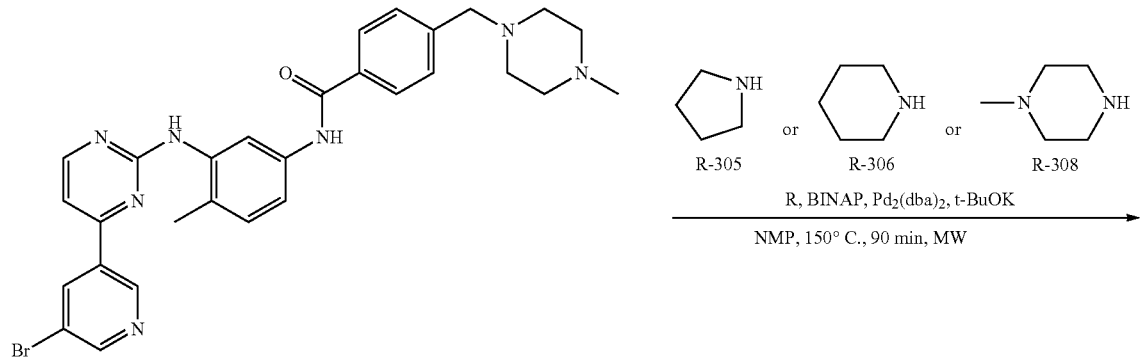

5

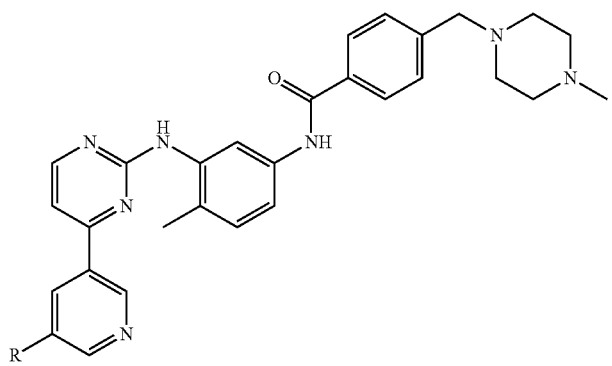

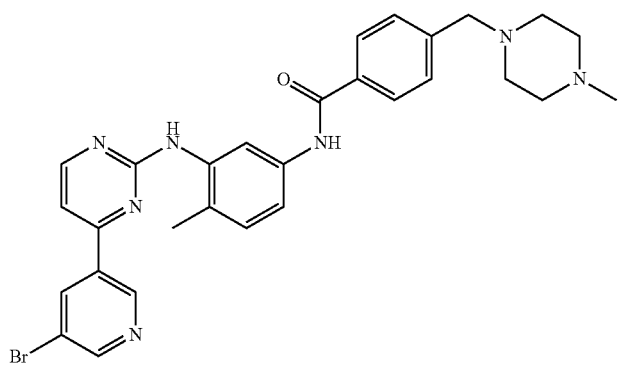
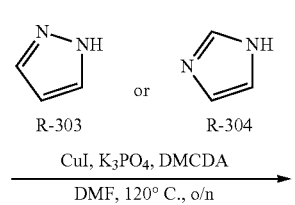
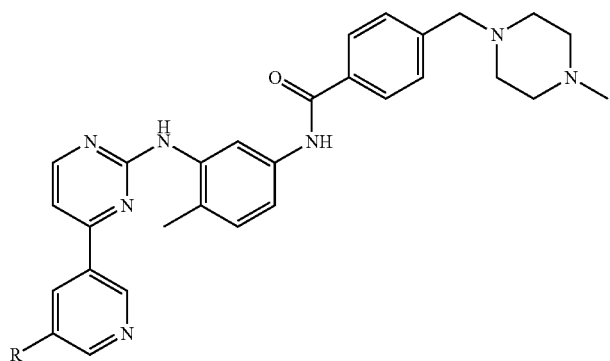
Compounds 303 and 304 were prepared using this general procedure.
Synthesis of Compound 107
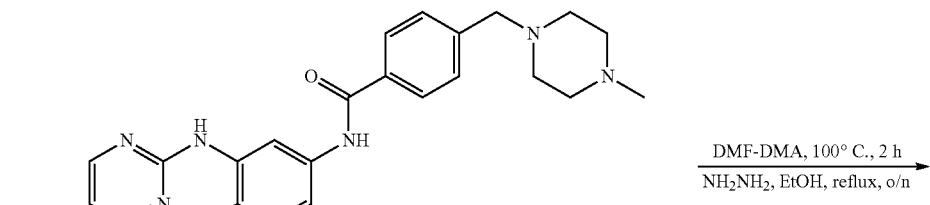
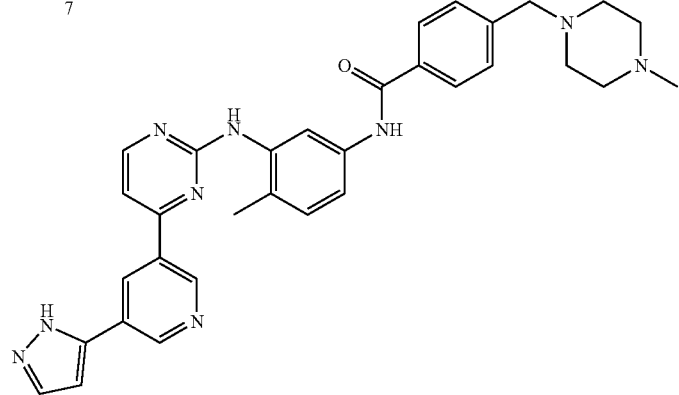

A solution of 7 (150 mg, 0.28 mmol) in DMF-DMA (3 mL) was stirred at 100° C. for 2 hours. Then the solution was cooled to room temperature and the solvent removed at reduced pressure. The crude residue was dissolved in EtOH (10 mL), and hydrazine (45 mg, 1.40 mmol) was added. The resulting mixture was heated to reflux overnight. The solvent was cooled to room temperature and concentrated in vacuo. The residue was purified by prep-HPLC to afford 107 (20 mg, 13%) as a solid.

Synthesis of Compound 207

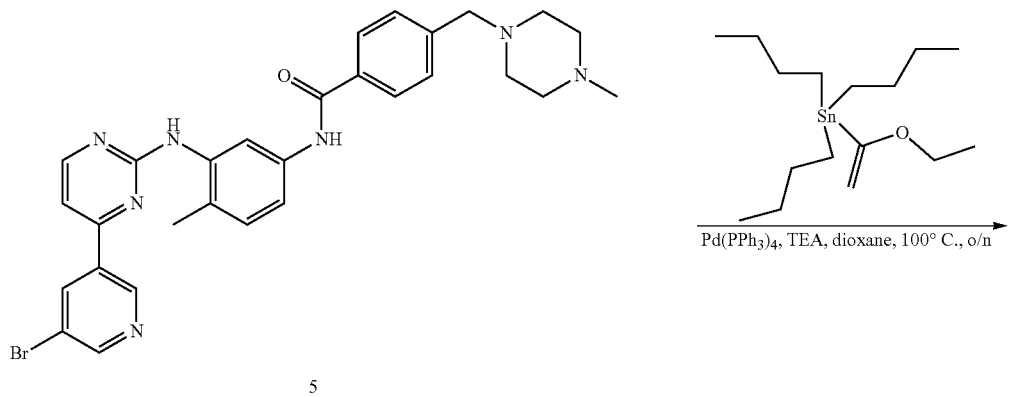

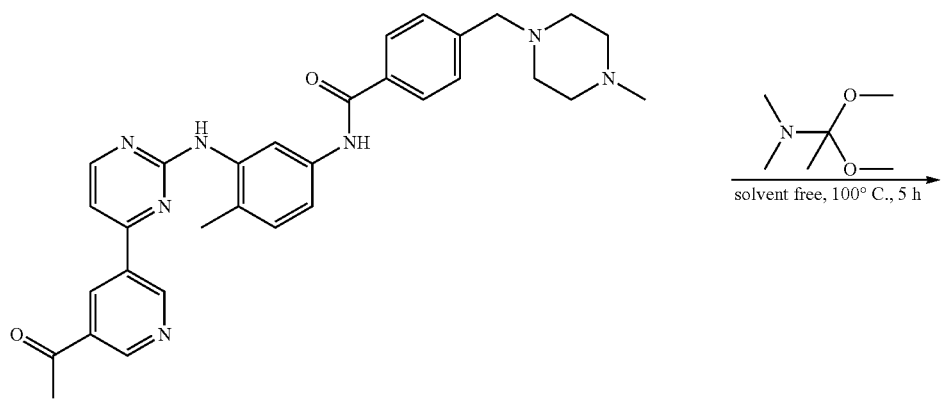

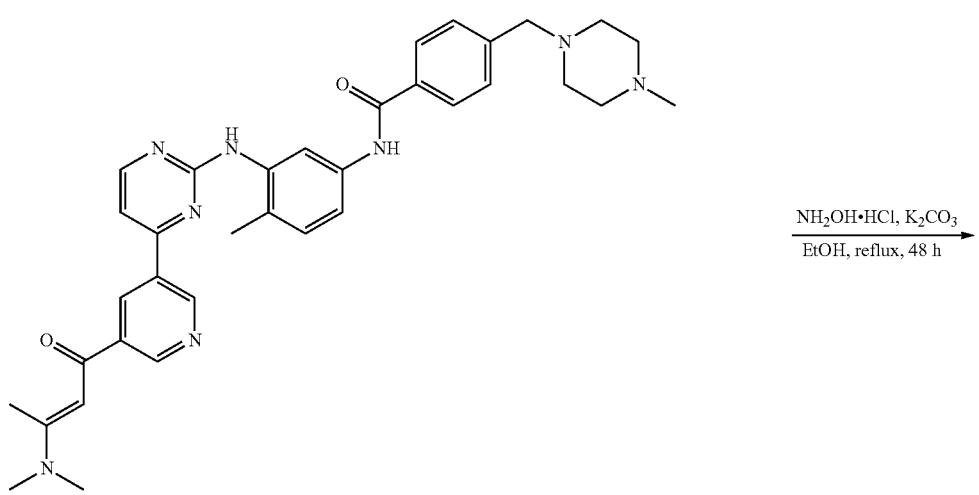

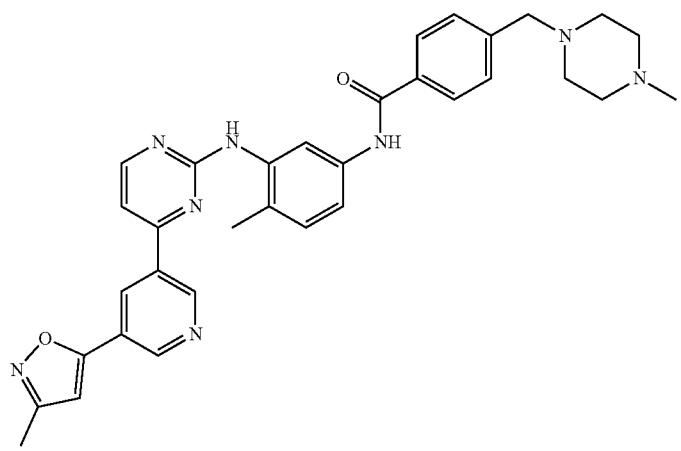

207

A solution of 7 (200 mg, 0.37 mmol) in DMA-DMA (4 mL) was heated to 100° C. and stirred for 2 hours. The excess DMA-DMA was evaporated in vacuo, and the residue was dissolved in ethanol (10 mL), to this solution was added K$_2$CO$_3$ (255 mg, 1.85 mmol) and hydroxylamine hydrochloride (77 mg, 1.11 mmol). The resulting mixture was refluxed overnight. After cooling, the mixture was filtered through celite and the filtrate was concentrated in vacuo. The residue was purified by prep-HPLC to afford compound 207 (18 mg, 8%) as a solid.

Synthesis of Compounds 870, 880, 8300, 831, 832

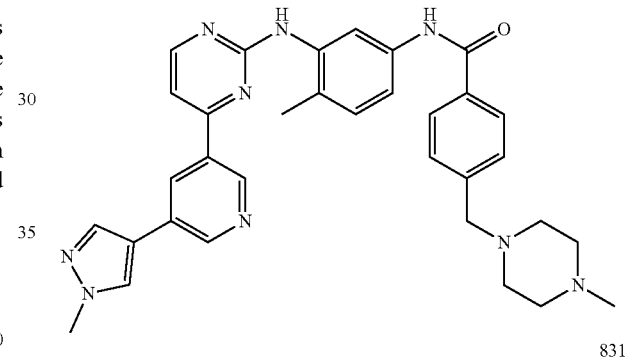

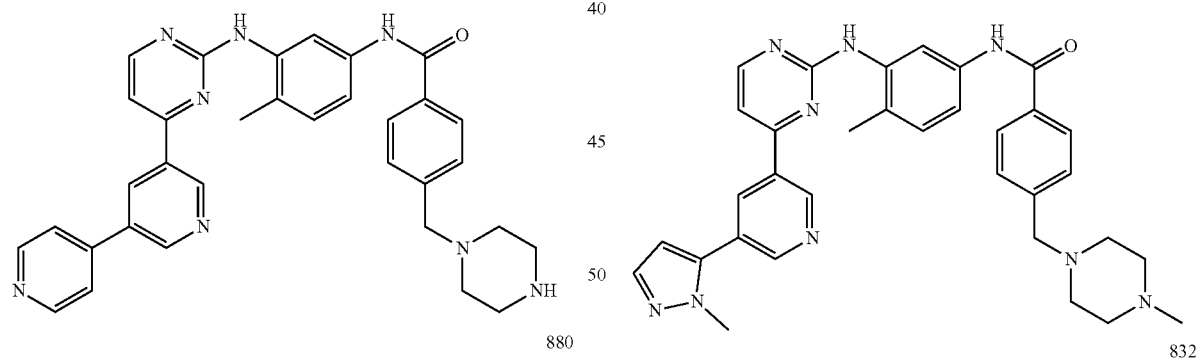

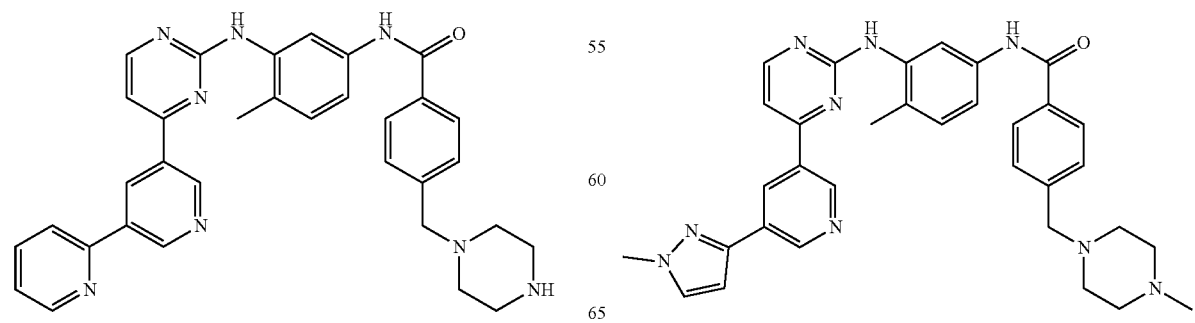

Methods

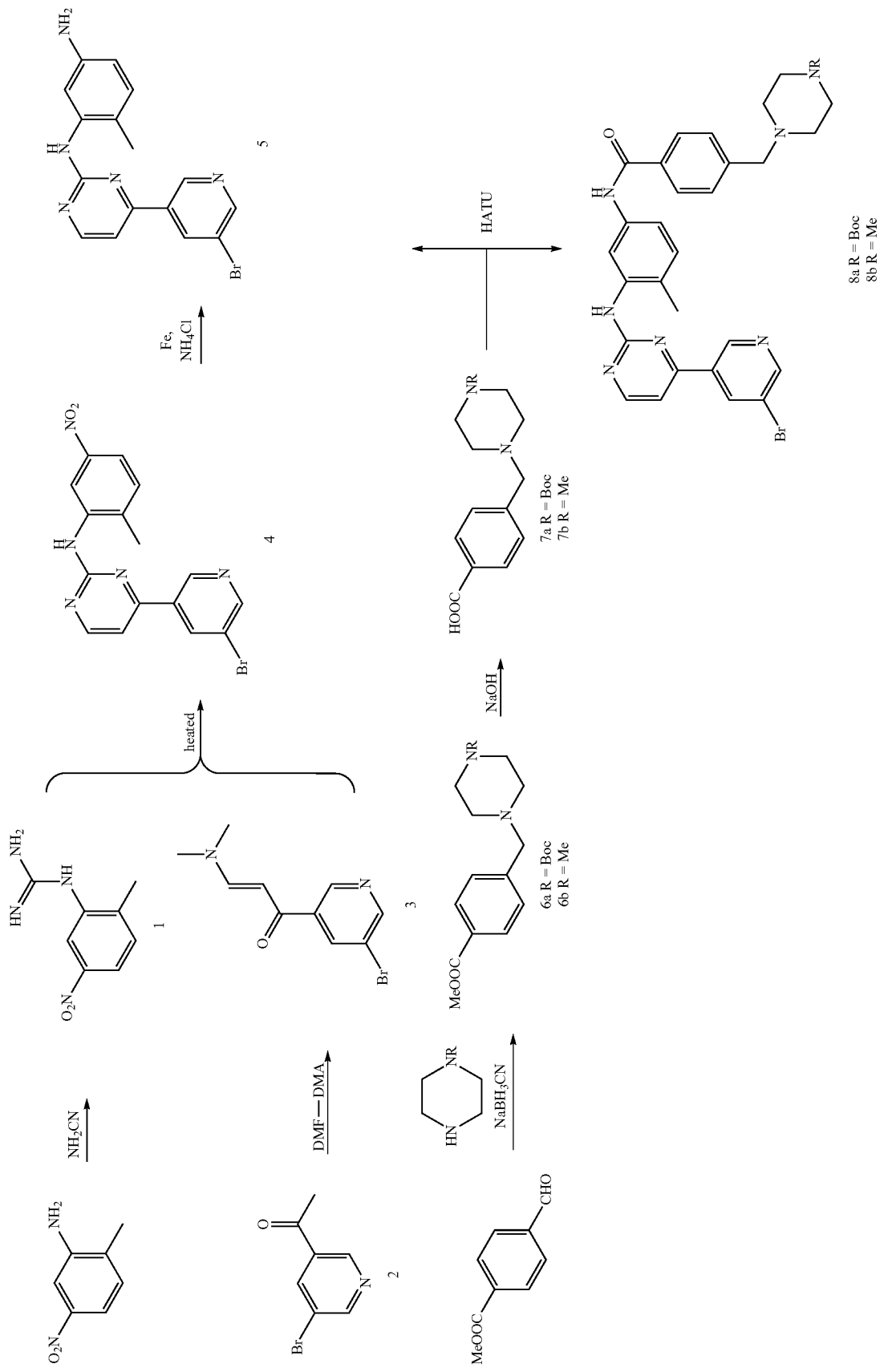

-continued
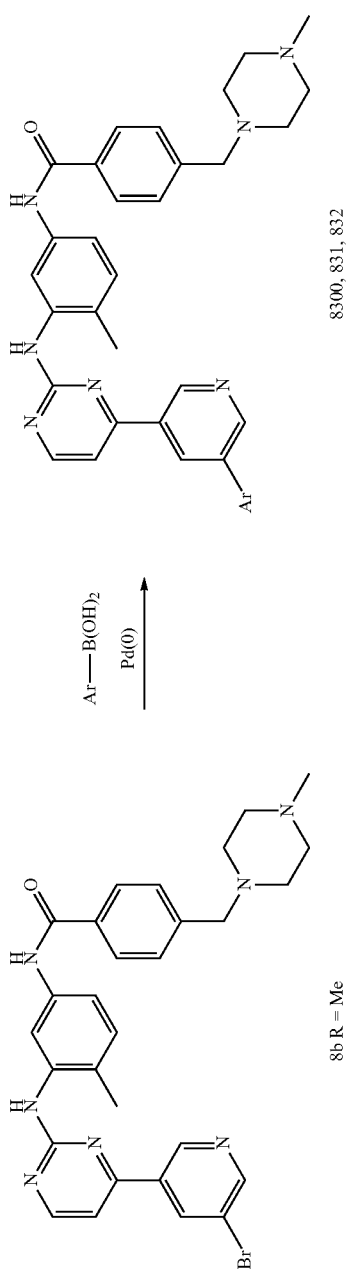
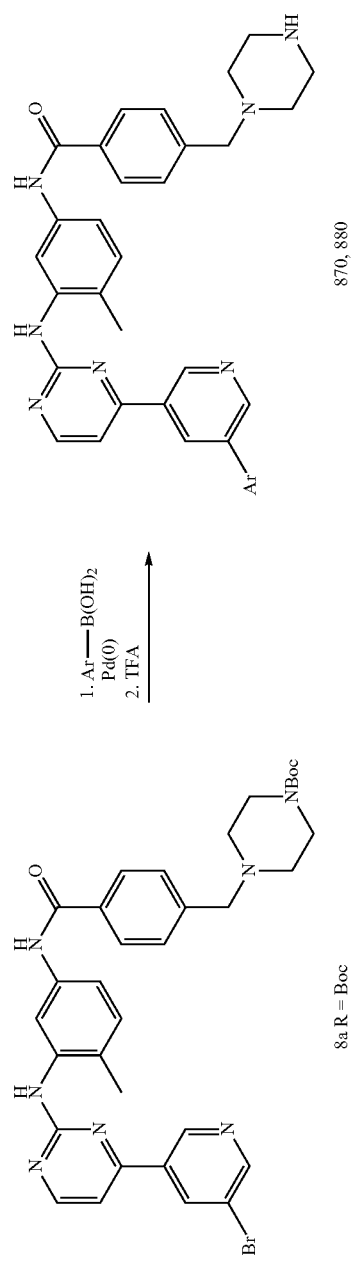

1-(2-Methyl-5-nitrophenyl)guanidine (1)

A mixture of 2-methyl-5-nitroaniline (152 g, 1.0 mol), cyanamide (247 mL, 6.0 mol) and isopropyl alcohol (1000 mL) were placed in a 3 L flask. The mixture was heated to 80° C. Concentrated hydrochloric acid (57 mL) was slowly added dropwise over 80 min. The reaction mixture was stirred for 1 h while maintaining the temperature at 80° C. Another portion of concentrated hydrochloric acid (144 mL) was added dropwise at 80° C. The reaction mixture was then stirred for 12 h at 100° C. The mixture was cooled to room temperature and treated with aqueous NaOH (2.5 N, 1200 mL). The resulting solid was collected by filtration, washed with isopropyl alcohol (500 mL) and dried to afford compound 1 (145 g, 76% yield).

(E)-1-(5-Bromopyridin-3-yl)-3-(dimethylamino)prop-2-en-1-one (3)

A mixture of 3-acetyl-5-bromopyridine (126.7 g, 0.633 mol) and DMF-DMA (84 g, 70.6 mmol) was heated under reflux for 1 h. The mixture was cooled to room temperature and then directly purified by silica gel column chromatography. The resulting crude product after concentration was washed with diethyl ether (200 mL) and dried to afford compound 3 (122 g, 75.5% yield) as yellow crystals.

4-(5-Bromopyridin-3-yl)-N-(2-methyl-5-nitrophenyl)pyrimidin-2-amine (4)

A mixture of compound 1 (10.0 g, 51.5 mmol) and compound 3 (12.9 g, 50.8 mmol) in 2-propanol (150 mL) was heated under reflux for 18 h. The mixture was cooled to room temperature and the resulting precipitate was collected by filtration, washed with diethyl ether (100 mL) and dried to afford compound 4 (13.2 g, 67% yield) as pale yellow crystals.

$N^1$-(4-(5-Bromopyridin-3-yl)pyrimidin-2-yl)-6-methylbenzene-1,3-diamine (5)

A mixture of iron 5.0 8 g, 907 mmol), $NH_4Cl$ (970 mg, 18.1 mmol) and $SiO_2$ (3 g) in ethanol/water (1:1, 140 mL) was heated at 55° C. for 10 min. Then a suspension of compound 4 (7.0 g, 18.1 mmol) in THF (70 mL) was added. The reaction mixture was stirred under reflux for 1 h and cooled to room temperature. The mixture was poured into water (100 mL) and then extracted with ethyl acetate (100 mL×2). The combined organic layers were washed with brine and water, dried over anhydrous sodium sulfate and concentrated to afford compound 5 (5.88 g, 91% yield) as yellow solid.

tert-Butyl 4-(4-(methoxycarbonyl)benzyl)piperazine-1-carboxylate (6a)

TFA (10 mL) was added dropwise to a mixture of methyl 4-formylbenzoate (20 g, 121 mmol) and tert-butyl piperazine-1-carboxylate (25 g, 134 mmol) in acetonitrile (400 mL) at room temperature. The mixture was stirred for 1 h and $NaBH_3CN$ (8.32 g, 134 mmol) was added. The reaction mixture was stirred overnight at room temperature and water was added. The resulting mixture was extracted with ethyl acetate (100 mL×2). The combined organic layers were washed with brine and water, dried over anhydrous sodium sulfate and concentrated to afford compound 6a (14 g, 34.4% yield), which was used directly in the next step without further purification.

Methyl 4-(piperazin-1-ylmethyl)benzoate (6b)

Compound 6b was prepared from 1-methylpiperazine following the same procedure for 6a.

4-((4-(tert-Butoxycarbonyl)piperazin-1-yl)methyl)benzoic acid (7a)

A mixture of compound 6a (7.0 g, crude, 21 mmol) and LiOH—$H_2O$ (1.4 g, 31 mmol) in methanol/acetonitrile/water (100 mL, 1:2:2) was stirred 1 h at room temperature. The organic solvent was removed and the remaining aqueous solution was washed with ethyl acetate (100 mL) and then adjusted to pH=2-3 with 2N aqueous HCl. The resulting mixture was extracted with ethyl acetate (30 mL×2). The combined extracts were dried over anhydrous sodium sulfate and concentrated to afford compound 7a (3.0 g, 44.8% yield) as a white solid.

4-(Piperazin-1-ylmethyl)benzoicacid (7b)

Compound 7b was prepared from 6b following the same procedure for 7a tert-Butyl 4-(4-(3-(4-(5-Bromopyridin-3-yl)pyrimidin-2-ylamino)-4-methyl phenylcarbamoyl)benzyl)piperazine-1-carboxylate (8a)

A mixture of compound 5 (1.0 g, 2.81 mmol), compound 7a (0.98 g, 4.19 mmol), HATU (1.28 g, 3.37 mmol) in DMF (20 mL) was cooled to 0° C. and DIPEA (1.95 mL, 11.24 mmol) was added. The reaction mixture was allowed to warm to room temperature and stirred for 15 min. Saturated aqueous sodium bicarbonate (20 mL) was added and the resulting mixture was extracted with ethyl acetate (50 mL×2). The combined extracts were dried over anhydrous sodium sulfate and concentrated. The residue was purified by flash column chromatography on silica gel (petroleum ether/ethyl acetate=3:1 to 1:1) to afford compound 8a (1.29 g, 80% yield) as a yellow solid.

N-(3-(4-(5-Bromopyridin-3-yl)pyrimidin-2-ylamino)-4-methylphenyl)-4-(piperazin-1-ylmethyl)benzamide (8b)

Compound 8b was prepared from 7b following the same procedure for 8a.

General Procedure for the Final Compounds 8300, 831, 832: A mixture of compound 8a/b (1.0 eq), the corresponding boronic acid (1.0 eq), Pd(dppf)$Cl_2$ (cat.) and $Na_2CO_3$ (2.5 eq) in 1-4-dioxane and water (5:1) was stirred at 80° C. for 1 h under $N_2$. The mixture was cooled to room temperature and then diluted with ethyl acetate and water. The resulting mixture was filtered and the filtrate was separated. The aqueous phase was extracted with ethyl acetate. The combined organic phases were washed with brine, dried over anhydrous sodium sulfate and concentrated to dryness. The residue was purified by flash column chromatography on silica gel or prep-HPLC to afford compound of interest as a yellow solid.

870: To a mixture of compound 8a (100 mg, 0.152 mmol), pyridin-4-ylboronic acid (21 mg, 0.167 mmol), Pd(dppf)$Cl_2$ (15 mg, cat.) and $Na_2CO_3$ (40 mg, 0.608 mmol) in 1-4-dioxane (2.5 mL) and water (0.5 mL) was stirred at 80° C. for 1 h under $N_2$. The mixture was cooled to room temperature and then diluted with ethyl acetate (10 mL) and water (10 mL). The resulting mixture was filtered and the filtrate was separated. The aqueous phase was extracted with EtOAc (20 mL×2). The combined organic phases were washed with brine (20 mL×2), dried over anhydrous and concentrated to dryness. The residue was purified by flash column chromatography on silica gel (DCM/MeOH=100:1 to 20:1) to afford compound Boc-870 (100 mg) as a brown solid.

TFA (1 mL) was added to a solution of Boc-870 (100 mg, 0.152 mmol) in CH₂Cl₂ (4 mL) at 0° C. with stirring. The reaction mixture was stirred for 1 h and concentrated to dryness. The residue was treated with aqueous NaHCO₃ to adjust pH=9 and then extracted with ethyl acetate (5 mL×3). The combined organic layers were washed with water and brine, dried over anhydrous sodium sulfate and concentrated. The residue was purified by flash column chromatography on silica gel (DCM/MeOH=20:1 to 10:1) to afford compound 870 (66 mg, 78.4% yield) as an off-white solid.

880: Compound 880 was prepared from pyridin-2-ylboronic acid following the same procedure for 870.

Synthesis of 810, 820, 830, 840, 8150, 8170, 8190, 8200, 8220, 8250, 8260, 8270, 8280, 8290

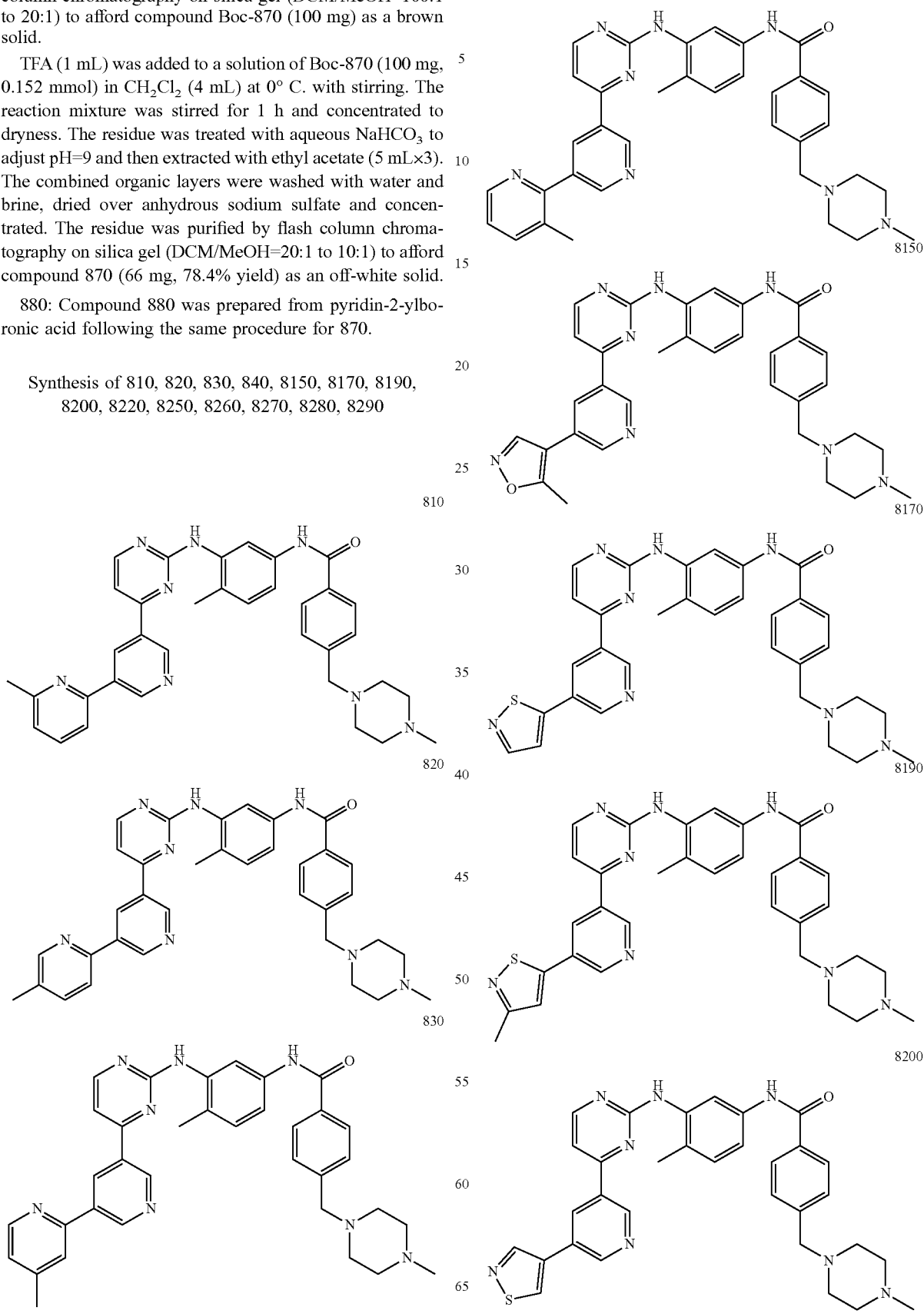

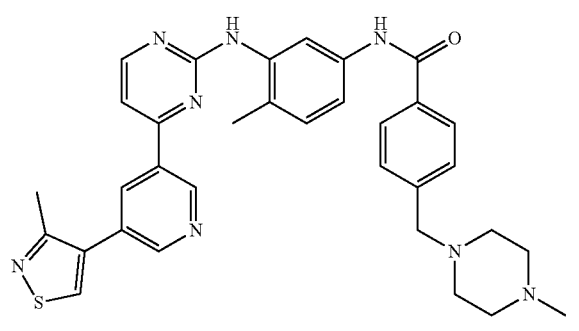
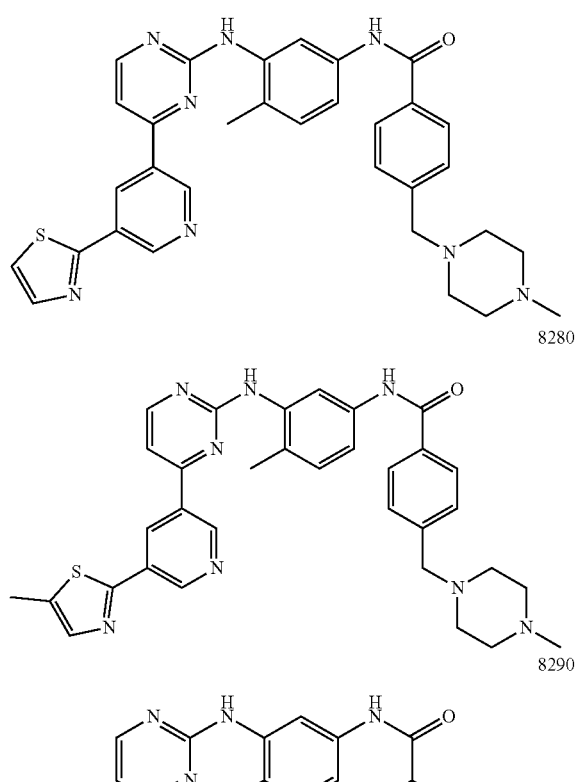
Methods
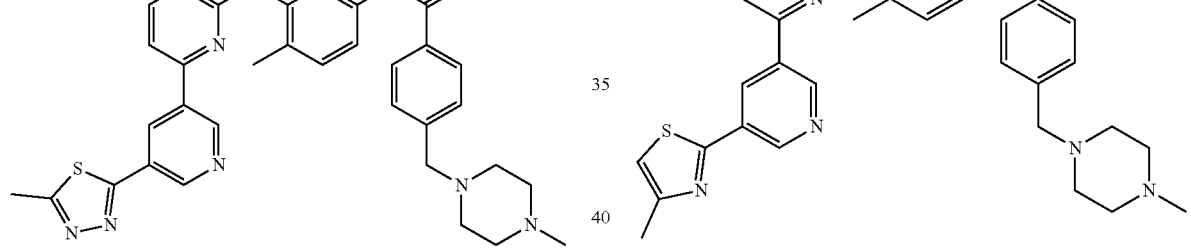
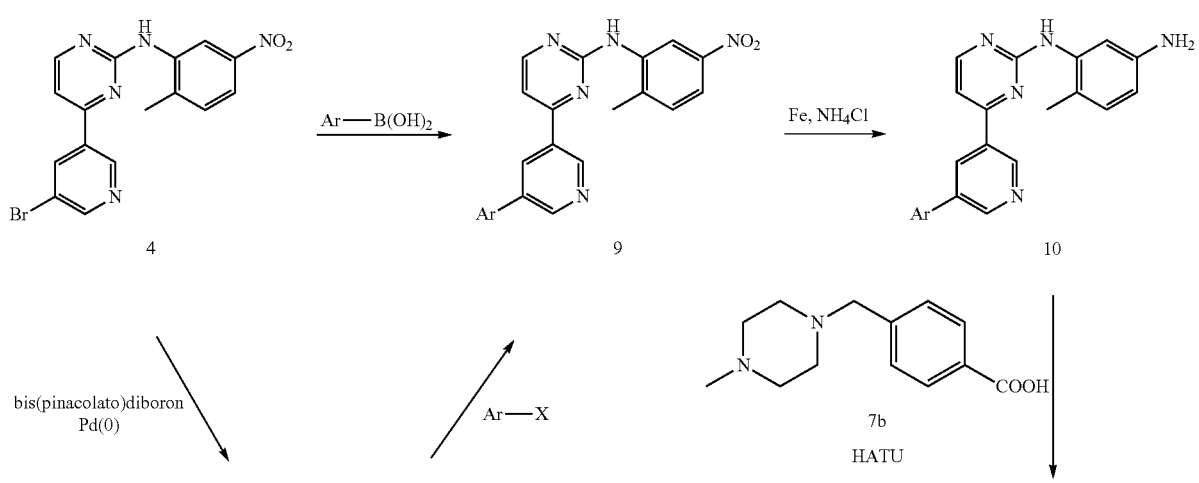

-continued

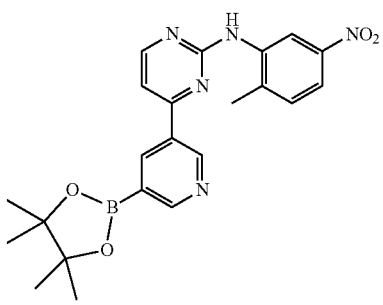

11

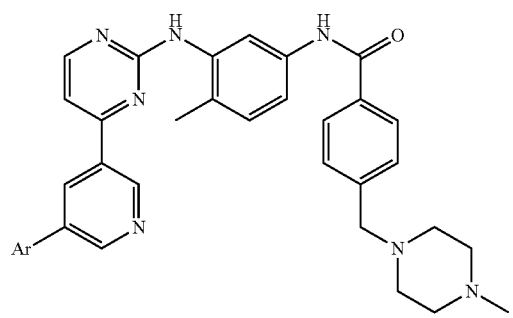

810, 820, 830, 840,
8150, 8170, 8190,
8200, 8220, 8250,
8260, 8270, 8280,
8290

General Procedure for Compound 9 from Compound 4 810, 820, 830, 840

To a mixture of compound 4 (1.0 eq), the corresponding boronic acid (1.0 eq), Pd(dppf)Cl$_2$ (cat.) and Na$_2$CO$_3$ (2.5 eq) in 1-4-dioxane and water (5:1) was stirred at 80° C. for 1 h under N$_2$. The mixture was cooled to room temperature and then diluted with ethyl acetate and water. The resulting mixture was filtered and the filtrate was separated. The aqueous phase was extracted with ethyl acetate. The combined organic phases were washed with brine, dried over anhydrous sodium sulfate and concentrated to afford compound 9, which was used in the next step without further purification.

N-(2-Methyl-5-nitrophenyl)-4-(5-(4,4,5,5-tetramethyl-1,3,2-dioxaborolan-2-yl)pyridin-3-yl)pyrimidin-2-amine (11)

A mixture of compound 4 (5.0 g, 12.95 mmol), bis(pinacolato)diboron (3.62 g, 14.25 mmol), Pd(dppf)Cl$_2$ (0.3 g, cat.) and KOAc (3.83 g, 38.87 mmol) in toluene (50 mL) was heated under reflex for 12 h under N$_2$. The mixture was cooled to room temperature and diluted with ethyl acetate (100 mL) and water (100 mL). The resulting mixture was filtered and the filtrate was separated. The aqueous phase was extracted with ethyl acetate (100 mL×2). The combined organic phases were washed with brine (30 mL), dried over anhydrous sodium sulfate and concentrated to dryness. The residue was purified by flash column chromatography on silica gel (Petroleum/EtOAc=20:1) to afford compound 11 (4.77 g, 84.3% yield) as a brown solid.

General Procedure for Compound 9 from Compound 11 8150, 8170, 8190, 8200, 8220, 8250, 8260, 8270, 8280, 8290

A mixture of Ar—X (1.0 eq), compound 11 (1.1 eq), Pd(dppf)Cl$_2$ (cat.) and Na$_2$CO$_3$ (3.0 eq) in 1-4-dioxane and water (5:1) was stirred at 80° C. for 1 h under N$_2$. The mixture was cooled to room temperature and diluted with ethyl acetate and water. The resulting mixture was filtered and the filtrate was separated. The aqueous phase was extracted with ethyl acetate and the combined organic phases were washed with brine, dried over anhydrous sodium sulfate and concentrated to afford compound 9, which was used in the next step without further purification.

General Procedure for Compound 10

A mixture of iron (5.0 eq), NH$_4$Cl (1.0 eq) and SiO$_2$ (2.0 eq) in ethanol/water (1:1) was heated at 55° C. for 10 min. Then a suspension of compound 9 (1.0 eq) in THF was added. The reaction mixture was stirred under reflux for 1 h and cooled to room temperature. The mixture was poured into water and then extracted with ethyl acetate. The combined organic layers were washed with brine and water, dried over anhydrous sodium sulfate and concentrated to afford compound 10 as a yellow solid.

General Procedure for the Final Compound

A mixture of compound 10 (1.0 eq), compound 7b (1.2 eq) and HATU (1.2 eq) in DMF (20 mL) was cooled to 0° C. and DIPEA (4.0 eq) was added. The reaction mixture was allowed to warm to room temperature and stirred for 15 min. Saturated aqueous sodium bicarbonate was added and the resulting mixture was extracted with ethyl acetate. The combined extracts were dried over anhydrous sodium sulfate and concentrated. The residue was purified by flash column chromatography on silica gel to afford the desired compound as a solid.

Synthesis of 806, 809, 8120, 8130, 8180, 8230, 8140

806

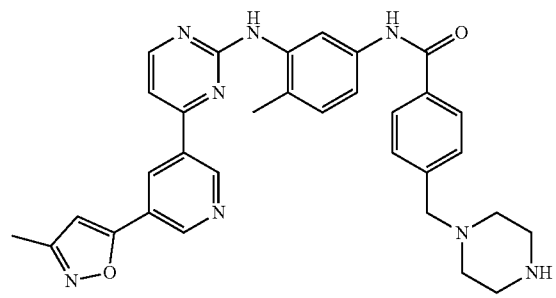

809

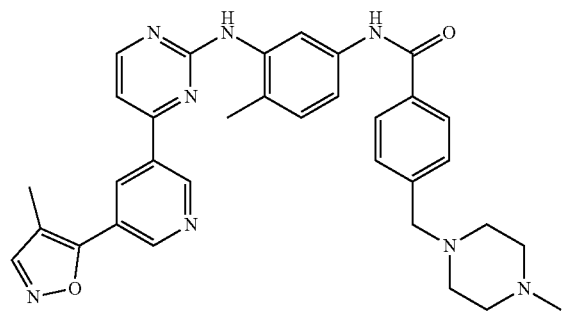

-continued
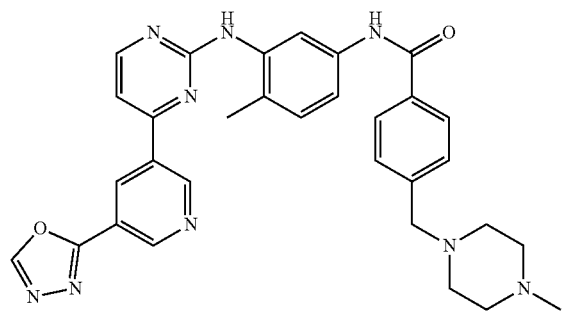
8120
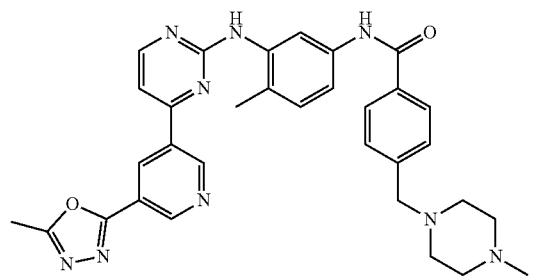
8130
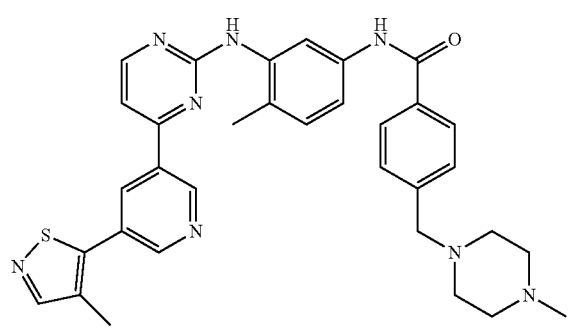
8180
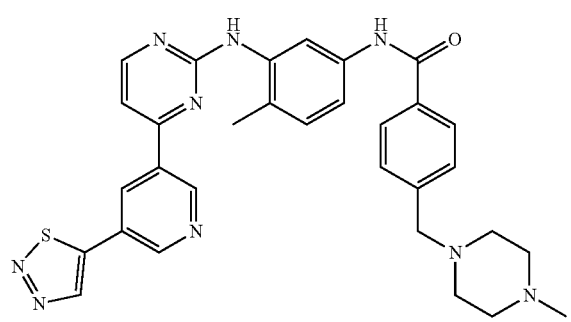
8230
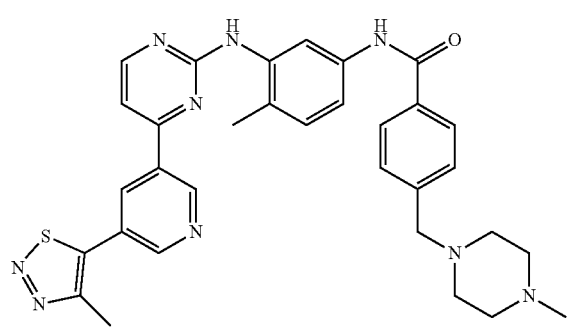
8240
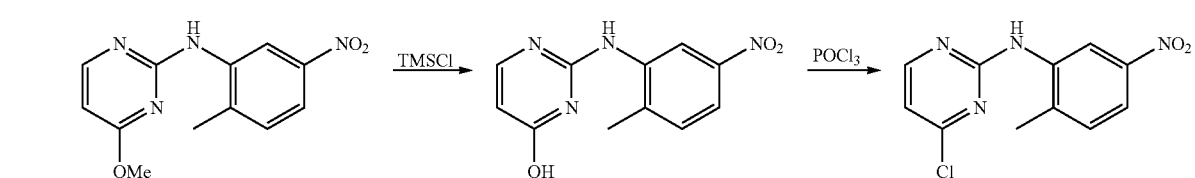
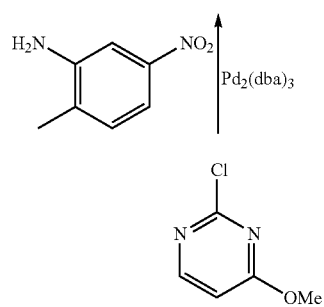
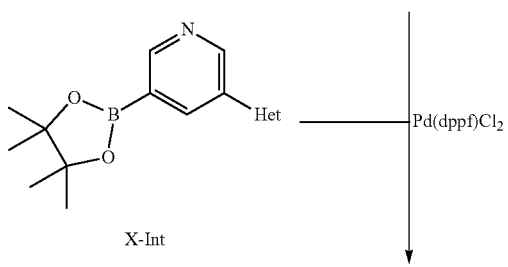

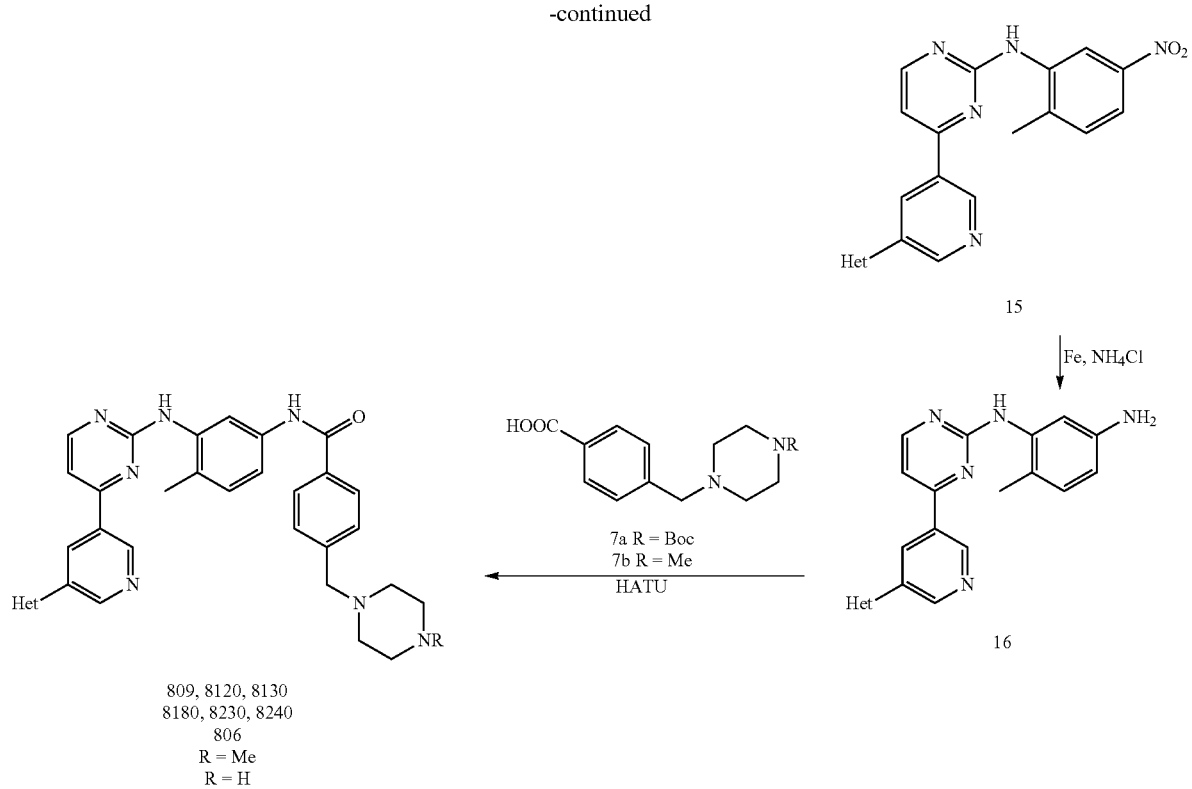

4-Methoxy-N-(2-methyl-5-nitrophenyl)pyrimidin-2-amine (12)

To a mixture of 2-chloro-4-methoxypyrimidine (9.54 g, 66 mmol), 2-methyl-5-nitrobenzenamine (10.0 g, 66 mmol), $Pd_2(dba)_3$ (1.0 g), S-Phos (1.0 g, 24.4 mmol), and $Cs_2CO_3$ (31.8 g, 99 mmol) in 1,4-dioxane/water (140 mL/60 mL) was heated at 110° C. overnight. The mixture was cooled to room temperature and then filtered through a pad of celite. The filtrate was diluted with ethyl acetate and washed with water. The organic phase was dried over anhydrous sodium sulfate and concentrated. The residue was purified by flash column chromatography on silica gel to afford compound 12 (12 g. 70.6% yield) as a light yellow solid.

2-(2-Methyl-5-nitrophenylamino)pyrimidin-4-ol (13)

A mixture of compound 12 (20 g, 77 mol), TMSCl (15 g, 136 mmol) and NaI (23.4 g, 156 mmol) in acetonitrile (400 mL) was heated at 120° C. overnight. The mixture was cooled to room temperature and 2N aqueous $Na_2CO_3$ (400 mL) and DCM (400 mL) were added. The organic layer was separated, washed with water, dried over anhydrous sodium sulfate and concentrated. The residue was purified by flash column chromatography on silica gel (DCM/MeOH=200:1) to afford compound 13 (12.1 g, 64% yield) as a light yellow solid.

4-Chloro-N-(2-methyl-5-nitrophenyl)pyrimidin-2-amine (14)

A mixture of compound 13 (2 g, 8.13 mmol) and DMF (5 drops) in $POCl_3$ (40 mL) was heated under reflux for 2 h. The mixture was cooled to room temperature and most of $POCl_3$ was removed. The residue was poured into aqueous NaOH (100 mL) carefully and the resulting mixture was extracted with DCM (100 mL×2). The combined organic layers were washed with brine and water (100 mL), dried over anhydrous sodium sulfate and concentrated to afford compound 14 (2.0 g, 93% yield) as a yellow solid.

General Procedure for Compound 15

A mixture of compound 14 (1.0 eq), PTC-1480-X-Int (1.0 eq), Pd(dppf)Cl$_2$ (cat.) and $K_2CO_3$ (3.0 eq) in 1-4-dioxane (20 mL) and water (20 mL) was heated under reflux for 12 h under $N_2$. The mixture was cooled to room temperature and diluted with ethyl acetate and water. The resulting mixture was filtered and the filtrate was separated. The aqueous phase was extracted with ethyl acetate. The combined organic phases were washed with brine, dried over anhydrous sodium sulfate and concentrated to dryness. The residue was purified by flash column chromatography on silica gel (DCM/MeOH=200:1) to afford compound 15 as a yellow solid.

General Procedure for Compound 16

To a mixture of iron (1.0 eq), $NH_4Cl$ (2.0 eq) and $SiO_2$ (cat) in ethanol/water (1:1) was heated at 55° C. for 10 min. Then a suspension of compound 15 (2.0 eq) in THF was added. The reaction mixture was stirred under reflux for 1 h and cooled to room temperature. The mixture was poured into water and then extracted with ethyl acetate. The combined organic layers were washed with brine and water, dried over anhydrous sodium sulfate and concentrated to afford compound 16.

Procedure for 806

A mixture of compound 16 (Het=3-methylisoxazol-5-yl, 150 mg, 0.42 mmol), compound 7a (134 mg, 0.42 mmol) and HATU (159 mg, 0.42 mmol) in DMF (2 mL) was cooled to 0° C. and DIPEA (217 mg, 1.68 mmol) was added. The reaction mixture was allowed to warm to room temperature and stirred for 15 min. Saturated aqueous sodium bicarbonate was added and the resulting mixture was extracted with ethyl acetate. The combined extracts were dried over anhydrous sodium sulfate and concentrated. The residue was purified by flash column chromatography on silica gel (Petroleum ether/ethyl acetate=1:1 to ethyl acetate) to afford compound Boc-806 (180 mg, 65.2% yield) as a solid.

HCl/EtOAc (2N, 1 mL) was added to a solution of Boc-806 (97 mg, 0.147 mmol) in EtOAc (1 mL) at 0° C. with stirring. The reaction mixture was stirred for 1 h and the resulting precipitate was collected by filtration, washed with DCM and dried to afford compound 806 (HCl salt, 80 mg, 100% yield) as a yellow solid.

General Procedure 806, 809, 8120, 8130, 8180, 8230 and 8240

A mixture of compound 16 (1.0 eq), compound 7b (1.0 eq) and HATU (1.0 eq) in DMF (2 mL) was cooled to 0° C. and DIPEA (4.0 eq) was added. The reaction mixture was allowed to warm to room temperature and stirred for 15 min. Saturated aqueous sodium bicarbonate was added and the resulting mixture was extracted with ethyl acetate. The combined extracts were dried over anhydrous sodium sulfate and concentrated. The residue was purified by flash column chromatography on silica gel (DCM/MeOH=20:1) to afford final compound as a yellow solid.

Example 2: Inhibition of Abelson Protein Kinases c-Abl1, c-Abl2 and c-Kit and Comparison to Imatinib, the Active Ingredient in Gleevec®

| Cpd | Abl1 (nM) | Abl2 (nM) | c-Kit (nM) |
|---|---|---|---|
| 101 | 232.35 | 224.57 | 6.80 |
| 102 | 95.33 | 169.62 | 6.70 |
| 103 | 200.41 | 212.18 | 7.70 |
| 107 | 45.17 | 66.95 | 7.20 |
| 108 | 40.53 | 85.88 | 7.40 |
| 113 | 35.00 | 50.11 | 7.50 |
| 114 | 101.53 | 142.60 | 32.40 |
| 115 | 107.81 | 202.79 | 8.90 |
| 116 | 91.06 | 160.89 | 11.60 |
| 117 | 29.13 | 34.99 | 5.70 |
| 118 | 37.16 | 51.00 | 8.40 |
| 119 | 117.66 | 44.68 | 4.00 |
| 201 | 193.18 | 514.16 | 19.30 |
| 202 | 403.88 | 701.00 | 31.10 |
| 203 | 250.56 | 711.96 | 47.10 |
| 207 | 30.19 | 73.73 | 12.20 |
| 303 | 162.15 | 349.36 | 18.90 |
| 305 | 397.83 | 631.35 | 9.20 |
| 309 | 174.37 | 149.18 | 14.00 |
| 401 | 167.28 | 178.63 | 12.40 |
| 402 | 183.14 | 207.42 | 11.10 |
| 404 | 100.32 | 116.17 | 5.80 |
| 405 | 107.09 | 150.43 | 5.90 |
| 806 | 84 | 152 | 13 |
| 809 | 47 | 77 | 7.8 |
| 820 | 84 | 173 | 10 |
| 830 | 34 | 51 | 6.0 |
| 832 | 53 | 77 | 4.0 |
| 880 | 203 | 341 | 12 |
| 8120 | 476 | 783 | 27 |
| 8130 | 323 | 423 | 44 |
| 8170 | 128 | 182 | 11 |
| 8180 | 369 | 303 | 13 |
| 8190 | 97 | 91 | 9.7 |
| 8200 | 96 | 131 | 4.3 |
| 8230 | >1000 | >1000 | 37 |
| 8240 | >1000 | >1000 | 39 |
| 8250 | 71 | 216 | 15 |
| 8260 | 41 | 236 | 16 |
| 8270 | 53 | 100 | 4.9 |
| 8280 | 57 | 104 | 6.2 |
| 8290 | 51 | 137 | 5.7 |
| 8300 | 40 | 39 | 5.2 |
| imatinib | 828.3 | 1000 | 30.7 |

Measurement of c-Abl1, c-Abl2 and c-Kit IC50 values

Kinase base buffer (50 mM HEPES, pH 7.5 0.0015% Brij-35; 10 mM MgCl$_2$ 2 mM DTT) and Stop buffer (100 mM HEPES, pH 7.5 0.015% Brij-35; 0.2% Coating Reagent (50 mM EDTA) are prepared. Test compound is diluted in 100% DMSO to 50-times the desired final inhibitor concentration (the Stock Solution) and serially diluted in half-log increments resulting in final concentrations 250 μM to 75 μM, 25 μM, 7.5 μM, 2.5 μM, 0.75 μM, 0.25 μM, 75 nM, 25 nM, 7.5 nM in DMSO. 10 μl of each compound is placed in a 96-well plate as the intermediate plate. 90 μl of Kinase Buffer is added to each well to prepare the intermediate plate. Mix the compounds in intermediate plate for 10 min on shaker. For the assay of enzyme inhibitions, 5 μl of each well from the intermediate plate is transferred to a 384-well plate in duplicates, 10. Then 10 μl of 2.5× enzyme solution is added to each well of the 384-well assay plate and incubated for 10 min. Then enzyme substrate is added as 10 μl of 2.5×FAM-labeled peptide+ATP solution to each well of the 384-well assay plate The reaction is allowed to proceed at 28° C. and quenched with the addition of 25 μl of stop buffer. The release of fluorescent FAM is quantitated as Percent inhibition=(max-conversion)/(max-min)*100. "max" stands for DMSO control; "min" stands for low control. Data are fit in XLFit excel add-in version 4.3.1 to obtain IC50 values. Equation used is: Y=Bottom+(Top-Bottom)/(1+(IC50/X)^HillSlope)

Example 3: Inhibition Profile of a 500 nM Solution of Test Compounds Against 14 Protein Kinases Kinase base buffer (50 mM HEPES, pH 7.5 0.0015% Brij-35; 10 mM MgCl$_2$ 2 mM DTT) and Stop buffer (100 mM HEPES, pH 7.5 0.015% Brij-35; 0.2% Coating Reagent (50 mM EDTA) are prepared. Test compound is diluted in 100% DMSO to 50-times the desired final inhibitor concentration (the Stock Solution) in DMSO. 10 μl of each compound is placed in a 96-well plate as the intermediate plate. 90 μl of Kinase Buffer is added to each well to prepare the intermediate plate. Mix the compounds in intermediate plate for 10 min on shaker. For the assay of enzyme inhibitions, 5 μl of each well from the intermediate plate is transferred to a 384-well plate in duplicates, 10. Then 10 μl of 2.5× enzyme solution is added to each well of the 384-well assay plate and incubated for 10 min. Then enzyme substrate is added as 10 μl of 2.5× FAM-labeled peptide+ATP solution to each well of the 384-well assay plate The reaction is allowed to proceed at 28° C. and quenched with the addition of 25 μl of stop buffer. The release of fluorescent FAM is quantitated as Percent inhibition=(max-conversion)/(max-min)*100. "max" stands for DMSO control; "min" stands for low control. Convert conversion values to inhibition values. Percent inhibition=(max-conversion)/(max-min)*100. "max" stands for DMSO control; "min" stands for low control.

TABLE 1

| Cpd | YES | PDGFRa | LCK | SRC | ABL | FLT3 | KIT | PDGFRb | FGR | LYNA | ARG/Abl2 | FES | FYN | JNK2 |
|---|---|---|---|---|---|---|---|---|---|---|---|---|---|---|
| 101 | 100 | 42 | 88 | 18 | 73 | 36 | 87 | 99 | 55 | 89 | 74 | 43 | 52 | 25 |
| 102 | 99 | 39 | 91 | 19 | 83 | 32 | 99 | 99 | 67 | 88 | 75 | 42 | 55 | 26 |
| 103 | 101 | 42 | 91 | 25 | 71 | 28 | 92 | 98 | 60 | 91 | 71 | 38 | 54 | 17 |
| 107 | 101 | 59 | 95 | 28 | 91 | 51 | 99 | 101 | 82 | 93 | 87 | 28 | 69 | 1.7 |
| 108 | 100 | 56 | 94 | 34 | 91 | 73 | 100 | 101 | 80 | 93 | 88 | 67 | 66 | 36 |
| 113 | 100 | 61 | 94 | 37 | 92 | 25 | 98 | 101 | 85 | 95 | 91 | 26 | 75 | 18 |
| 114 | 100 | 34 | 77 | 18 | 84 | 20 | 99 | 99 | 81 | 91 | 78 | 17 | 72 | 18 |
| 115 | 100 | 53 | 90 | 29 | 83 | 22 | 96 | 99 | 78 | 93 | 76 | 20 | 67 | 17 |
| 116 | 100 | 48 | 94 | 29 | 87 | 8.4 | 93 | 101 | 83 | 93 | 76 | 19 | 67 | 5.9 |
| 117 | 99 | 74 | 97 | 55 | 94 | 13 | 95 | 99 | 90 | 97 | 91 | 24 | 86 | 14 |
| 118 | 99 | 66 | 95 | 35 | 92 | 61 | 93 | 101 | 84 | 96 | 88 | 38 | 77 | 14 |
| 119 | 99 | 67 | 98 | 53 | 83 | 90 | 95 | 100 | 86 | 97 | 90 | 47 | 82 | 42 |
| 201 | 99 | 45 | 91 | 18 | 72 | 30 | 91 | 98 | 67 | 87 | 55 | 49 | 53 | 6.1 |
| 202 | 100 | 46 | 87 | 16 | 64 | 19 | 85 | 98 | 64 | 87 | 50 | 27 | 47 | 19 |
| 203 | 100 | 29 | 88 | 17 | 72 | 31 | 77 | 95 | 59 | 82 | 54 | 21 | 43 | 17 |
| 207 | 100 | 54 | 95 | 30 | 94 | 19 | 88 | 99 | 79 | 92 | 85 | 31 | 72 | 19 |
| 303 | 100 | 33 | 87 | 13 | 79 | 25 | 87 | 100 | 58 | 86 | 62 | 31 | 45 | 4.7 |
| 305 | 100 | 16 | 80 | 10 | 62 | 20 | 98 | 100 | 47 | 80 | 50 | 47 | 25 | 4.4 |
| 309 | 101 | 25 | 84 | 13 | 77 | 13 | 96 | 99 | 59 | 87 | 79 | 31 | 44 | 24 |
| 401 | 100 | 40 | 88 | 18 | 76 | 24 | 98 | 99 | 67 | 90 | 81 | 19 | 50 | 23 |
| 402 | 100 | 29 | 86 | 19 | 72 | 31 | 96 | 100 | 65 | 89 | 75 | 23 | 48 | 21 |
| 404 | 100 | 47 | 91 | 21 | 82 | 24 | 97 | 100 | 75 | 90 | 83 | 32 | 56 | 34 |
| 405 | 101 | 33 | 90 | 16 | 80 | 29 | 95 | 100 | 68 | 90 | 80 | 33 | 52 | 28 |

TABLE 2

| Cpd | Abl2 | Abl1 | PDGFRa | PDGFRb | JNK1 | JNK2 | SRC | LCK | CKIT | FES | YES | FYN | LYNA | FLT3 | FGR |
|---|---|---|---|---|---|---|---|---|---|---|---|---|---|---|---|
| 810 | 59 | 65 | 99 | 98 | 25 | 48 | 20 | 83 | 85 | 23 | 44 | 71 | 93 | 26 | 57 |
| 820 | 76 | 85 | 99 | 98 | 12 | 29 | 23 | 88 | 87 | 32 | 56 | 73 | 91 | 61 | 64 |
| 830 | 87 | 92 | 100 | 99 | 23 | 52 | 38 | 93 | 92 | 22 | 63 | 81 | 97 | 44 | 77 |
| 831 | 60 | 48 | 100 | 97 | 15 | 17 | 12 | 82 | 82 | 23 | 25 | 57 | 87 | 38 | 34 |
| 832 | 81 | 88 | 100 | 100 | 24 | 16 | 28 | 93 | 91 | 24 | 66 | 79 | 106 | 58 | 80 |
| 840 | 30 | 38 | 99 | 92 | 24 | 56 | 15 | 50 | 73 | 35 | 25 | 64 | 77 | 69 | 24 |
| 870 | 60 | 60 | 100 | 97 | 17 | 37 | 17 | 70 | 82 | 39 | 23 | 58 | 83 | 73 | 38 |
| 880 | 61 | 71 | 100 | 100 | 28 | 48 | 15 | 70 | 87 | 35 | 33 | 64 | 80 | 62 | 46 |
| 8150 | 54 | 42 | 99 | 97 | 31 | 42 | 14 | 77 | 83 | 26 | 26 | 62 | 90 | 68 | 34 |
| 8170 | 73 | 78 | 100 | 98 | 32 | 40 | 25 | 88 | 86 | 67 | 49 | 70 | 93 | 79 | 68 |
| 8190 | 81 | 82 | 100 | 99 | 41 | 58 | 28 | 92 | 86 | 51 | 52 | 74 | 96 | 72 | 71 |
| 8200 | 75 | 78 | 98 | 97 | 41 | 54 | 22 | 92 | 85 | 52 | 50 | 65 | 100 | 68 | 63 |
| 8220 | 54 | 44 | 99 | 97 | 56 | 50 | 22 | 90 | 83 | 57 | 40 | 75 | 93 | 75 | 47 |
| 8250 | 68 | 87 | 100 | 98 | 15 | 8 | 20 | 87 | 80 | 37 | 45 | 74 | 85 | 68 | 63 |
| 8260 | 67 | 85 | 100 | 101 | 21 | 15 | 22 | 83 | 79 | 16 | 41 | 71 | 88 | 62 | 60 |
| 8270 | 80 | 91 | 99 | 98 | 41 | 36 | 33 | 91 | 88 | 60 | 60 | 83 | 104 | 78 | 81 |
| 8280 | 80 | 90 | 100 | 99 | 23 | 14 | 28 | 82 | 89 | 32 | 53 | 76 | 98 | 54 | 78 |
| 8290 | 75 | 86 | 100 | 100 | 33 | 23 | 26 | 87 | 88 | 36 | 55 | 76 | 98 | 63 | 75 |
| 8300 | 89 | 92 | 99 | 98 | 35 | 30 | 45 | 97 | 88 | 19 | 63 | 90 | 108 | 61 | 81 |

Example 4: JCV Antiviral Potency and Therapeutic Index for Selected Compounds

TABLE 3

| Compound | Anti-JCV potency relative to imatinib ($EC_{50}^{Imatinib}$:$EC_{50}^{Novel}$) | Fold Improvement in Therapeutic Index ($TI^{Novel}$:$TI^{Imatinib}$) |
|---|---|---|
| 102 | 1.9 | 0.71 |
| 103 | 7.7 | >3.3 |
| 107 | 2.4 | 0.4 |
| 108 | 0.71 | 0.15 |
| 113 | 0.52 | 0.14 |
| 114 | Inactive | — |
| 117 | Inactive | — |
| 118 | <0.1 | <0.15 |
| 207 | 32.7 | >13.3 |
| 309 | 2.7 | 1 |
| 809 | 40 | >167 |
| 830 | 1.5 | >6.3 |
| 832 | 2.2 | >9.2 |
| 8190 | 9.4 | >39 |
| 8250 | 0.79 | >3.3 |
| 8270 | 5.7 | >24 |
| 8280 | 11.2 | >47 |
| 8290 | 2.7 | >11.3 |
| imatinib | 1 | 1 |

$EC_{50}$ was measured in triplicate with a multiplicity of infection of 0.02 over 7 days in Cos7 cells using the laboratory strain MAD-1, originally derived from the brain of PML patients. $EC_{50}$ was computed using PRISM and quality of fit regression coefficients >0.85 for each case. Relative antiviral potency was computed relative to the $EC_{50}$ of imatinib. Relative therapeutic index was computed by measuring the cell cytotoxicity $CC_{50}$:$EC_{50}$ ratio to calculate the Therapeutic Index (TI) with drug titration between 2 nM and 20 μM.

With respect to compound 118, only an upper limit to $EC_{50}$ could be calculated because 118 had little antiviral activity and poor quality data fit. With respect to compounds 103, 207, 809, 830, 832, 8190, 8250, 8270 and 8280, only the lower limit of relative TI could be calculated because the drug substance showed no toxicity up to 20 μM. The absolute value of $EC_{50}$ for imatinib was measured as 4.91 μM.

Example 5: Anti-Cancer Potency of Selected Compounds Against Mutant c-Kit Proteins Associated with Gastrointestinal Stromal Tumor 96 well plates were created using an HP D300 programmable digital dispensing tool (Hewlett-Packard). 10 mM drug stocks in DMSO were titrated into each well and each schematic plate map was recorded. Doses ranged from 3 nM to 1000 nM, depending upon the drug and experiment. Imatinib was used as a control drug and loaded on the plate in the same concentrations as for the test compounds. Media with DMSO at the highest concentration of the compounds was used as a negative control. These pre-made plates with dispensed drug and media were then frozen at −20° C. until used. Plates were warmed before cells were loaded. GIST cell lines with different genotypes were plated at 2000 cells per well in a 100 μl total volume. The plated cells were incubated for 72 hours, 5% $CO_2$, and 37° C. Proliferation/viability was measured using CellTiter-Glo® luminescent cell viability reagent which is based on the quantitation of ATP present in a cell. Plate was then read using GloMax® 96 microplate luminometer. Results are depicted in FIGS. 1A-1G.

Example 6: Western Blot Demonstrating that Selected Compounds Anti-Cancer Response is Due to a Block in Formation of Phosphorylated c-Kit (p-Kit)

Figure 2:
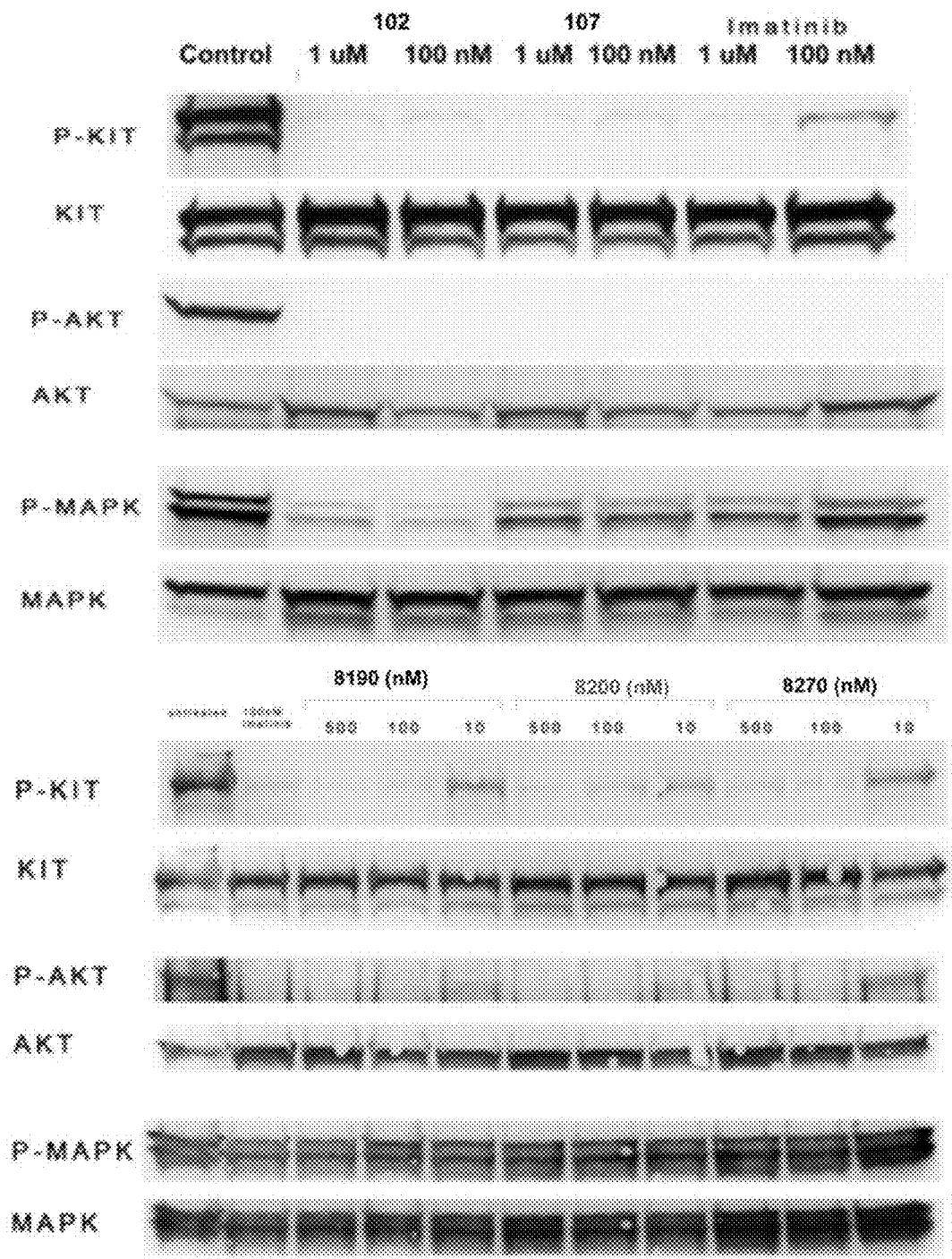
FIG. 2 depicts a Western blot showing the effect of imatinib and various compounds of the present invention on c-Kit phosphorylation, AKT phosphorylation, and MAPK phosphorylation.

Confluent T-25 flasks of GIST-related c-Kit protein containing the 557-558 deletion were expressed in T1 cells were treated with test compound for 90 minutes, 5% $CO_2$, 37° C. Untreated and imatinib treated cells served as controls. After lysis, 175 μg of whole cell lysate was subject to protein electrophoresis and transferred to nitrocellulose. KIT phosphorylation was visualized by probing the blot with P-KIT (Y719) antibody. AKT phosphorylation was visualized by probing with P-AKT. MAPK phosphorylation was visualized by probing with P-MAPK. After blot was striped, it was re-probed for total protein with KIT CD117 antibody, AKT antibody, and MAPK antibody, respectively. The blot is shown in FIG. 2.

Example 7: Anti-Cancer Potency of Selected Compounds Against Mutant BCR-Abl Proteins Associated with Chronic Myelogenous Leukemia

TABLE 4

| | IC50 (Ba/F3; nM) | | | | | | |
|---|---|---|---|---|---|---|---|
| | Parental | Native p210 | T315I | Y253H | E255K | E255V | F359V |
| 103 | 2923 | 20.23 | 2906 | 2594 | 196.2 | 1196 | 135.3 |
| 113 | 2065 | 12.17 | 2124 | 1434 | 46.89 | 738.6 | 161 |
| 207 | 2801 | 15.69 | 2796 | 2379 | 116.2 | 1290 | 128.8 |
| 820 | 2484 | 60.04 | 2303 | 2774 | 203.7 | 2670 | 260.3 |
| 860 | 4637 | 281.4 | 3429 | 7061 | 857 | 3130 | 792.8 |
| 890 | 6035 | 31.72 | 6553 | 5328 | 64.24 | 1447 | 213.4 |
| 8190 | 2237 | 58.54 | 2677 | 2098 | 389.7 | 997.2 | 236.5 |
| 8270 | 2521 | 18.82 | 2789 | 2269 | 45.9 | 1030 | 203.3 |
| 8280 | 2614 | 66.96 | 2770 | 2458 | 234.4 | 2389 | 251.4 |
| 8290 | 2583 | 98.75 | 2483 | 2872 | 80.4 | 1444 | 375.1 |
| 8300 | 2994 | 29.46 | 3775 | 1444 | 251.1 | 614.4 | 148.3 |
| 832 | 2485 | 9.939 | 2590 | 1584 | 90.86 | 661.1 | 46.7 |
| Imatinib | | 213 | | | | | |

Methods

The "parental" cell line refers to untransduced Ba/F3 cells grown in the presence of IL-3. The IC50s of the compounds against these cells are listed. To measure the IC50 values, pools of Ba/F3 cells harboring the specified isoform of BCR-ABL were established following retroviral transduction with MSCV puro BCR-ABL constructs and selected in the presence of puromycin. IL-3 was subsequently withdrawn from these populations.

For the experiment, exponentially growing cells were plated at a final concentration of 50,000 cells/mL in 10% RPMI containing 0.5% DMSO in a total volume of 1004, per well of a 96-well opaque plate. Final concentrations of each compound were 10 μM, 1 μM, 100 nM, 10 nM, 1 nM, 0.1 nM, 0 nM (plus a blank—media only). Each cell line and concentration was plated in triplicate for this single experiment. Plates were incubated for 48 hrs at 37° C. and read with Cell Titer Glo on a plate reader. Data was compiled with the Sensimax software; raw values were normalized to the untreated; averages were taken of the three normalized replicate wells and IC50 values were calculated via Prism 5.

Figure 3:
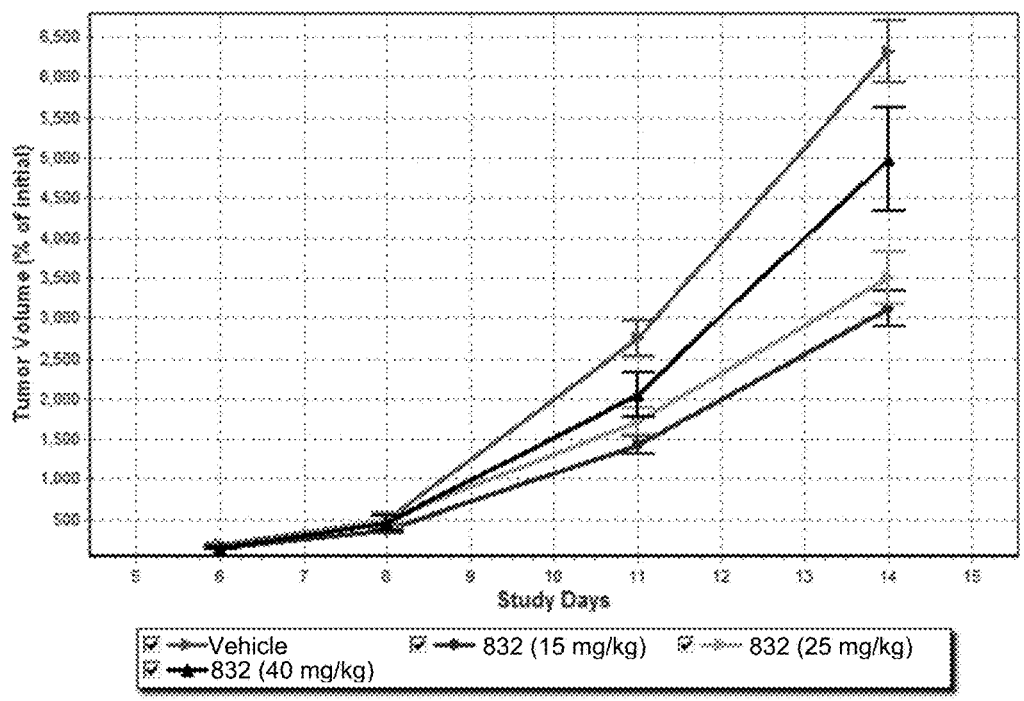
FIG. 3 shows the suppression of tumor growth for K562 cell BCR-Abl xenografts in NSG mice as a model of Chronic Myelogenous Leukemia.

Example 8: Suppression of Tumor Growth for K562 Cell BCR-Abl Xenograft in NSG Mice as a Model of Chronic Myelogenous Leukemia Methods:

5×10$^6$ K562 cells derived from a patient with CML and stably expressing the BCR-Abl transgene product were implanted subcutaneously in the hindlimb of NSG female mice, 7-9 weeks of age. The tumor was allow to develop to approximately 100 mm$^3$ prior to initiation of once per day (Q.D.) dosing at 0 (i.e. vehicle), 15 mg/kg, 25 mg/kg or 40 mg/kg for compound 832 by oral gavage in 50 mM sodium citrate as a vehicle, pH 3.5. Dosing was initiated at approximately day 6 after implantation and continued for 9 days. Measurement of tumor volume, veterinary observations and animal weight changes were used to determine the effectiveness of the drug with 5 mice per group. The results are depicted in FIG. 3.

All publications and patents cited herein are hereby incorporated by reference in their entirety.

Those skilled in the art will recognize, or be able to ascertain using no more than routine experimentation, many equivalents to the specific embodiments of the invention described herein. Such equivalents are intended to be encompassed by the following claims.

We claim:

1. A method of treating a mammal suffering from a bacterial infection or a viral infection, comprising administering to the mammal an effective amount of a compound of Formula (I) or a pharmaceutical composition thereof:

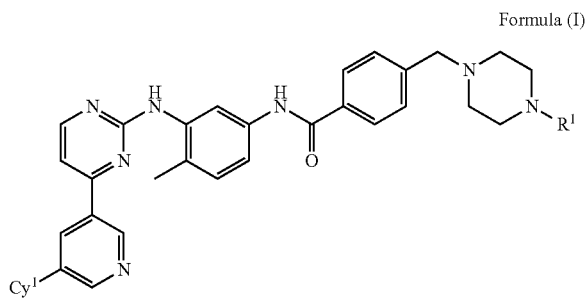

Formula (I)

wherein, independently for each occurrence,
R¹ is hydrogen, lower alkyl, —CH₃, —CDH₂, —CD₂H, or —CD₃; and
Cy¹ is heterocyclyl or substituted or unsubstituted 5-membered heteroaryl,
wherein the bacterial infection is caused by *Pseudomonas aeruginosa*, *Chlamydia trachomatis*, *Escherichia coli*, *Helicobacter pylori*, *Salmonella typhimurium*, *Shigella flexneri*, or *Mycobacterium tuberculosis*; and
the viral infection is caused by a Vaccinia virus, a variola virus, a polyoma virus, a Pox virus, a Herpes virus, cytomegalovirus, a human immunodeficiency virus, JC polyomavirus, BK polyomavirus, Simian virus 40, Monkeypox virus, Ebola virus, Marburg virus, Flavivirus, or West Nile virus.

2. The method of claim 1, wherein Cy¹ is selected from:

wherein, independently for each occurrence,
R² and R³ are selected from hydrogen, alkyl, amino, monoalkylamino, dialkylamino, cycloalkyl, halo, cyano, alkoxy, —C(O)OH, and —C(O)N(R⁴)(R⁴);
n is 1, 2, 3 or 4;
X is C(R⁴)₂, S, O, or NR⁴;
R⁴ is selected from hydrogen and substituted or unsubstituted alkyl, aralkyl, cycloalkyl, heterocyclyl, aryl, heteroaryl, heteroaralkyl, cycloalkylalkyl, or heterocyclylalkyl.

3. The method of claim 1, wherein Cy¹ is selected from:

wherein, independently for each occurrence,
R¹ is selected from hydrogen or lower alkyl;
R² and R³ are selected from hydrogen, alkyl, amino, monoalkylamino, dialkylamino, cycloalkyl, halo, cyano, alkoxy, —C(O)OH, and —C(O)N(R⁴)(R⁴);
R⁴ is selected from hydrogen and substituted or unsubstituted alkyl, aralkyl, cycloalkyl, heterocyclyl, aryl, heteroaryl, heteroaralkyl, cycloalkylalkyl, or heterocyclylalkyl.

4. The method of claim 1, wherein Cy¹ is a substituted or unsubstituted 5-membered heteroaryl.

5. The method of claim 4, wherein Cy¹ is selected from:

-continued

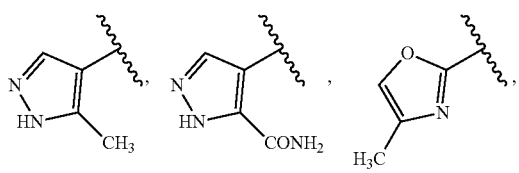

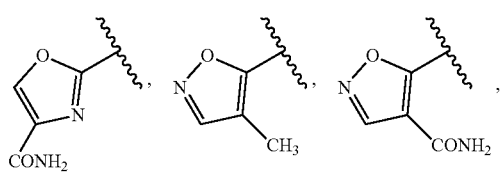

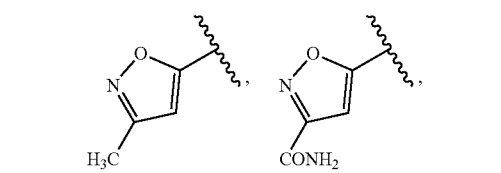

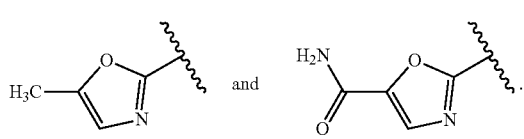

6. The method of claim 4, wherein Cy¹ is selected from:

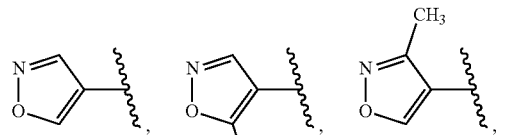

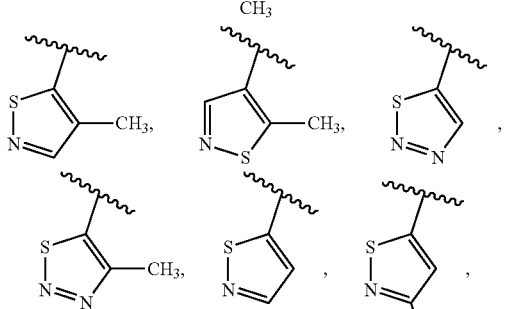

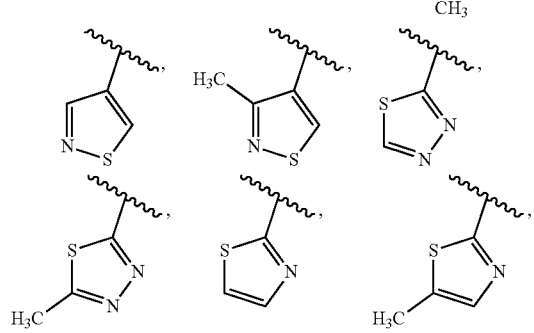

-continued

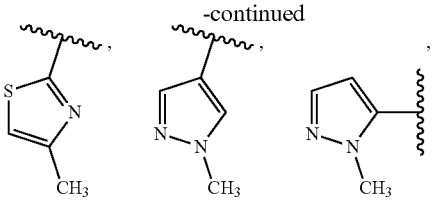

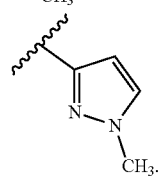

7. The method of claim 4, wherein Cy¹ is selected from:

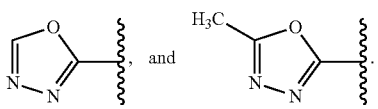

8. The method of claim 1, wherein Cy¹ is selected from:

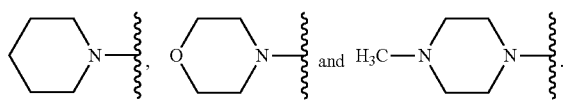

9. The method of claim 1, wherein R¹ is —CH₃, —CDH₂, —CD₂H, or —CD₃.

10. The method of claim 1, comprising administering to the mammal an effective amount of a pharmaceutical composition comprising the compound of claim 1.

11. The method of claim 10, wherein the pharmaceutical composition further comprises one or more pharmaceutically acceptable excipients.

12. The method of claim 1, wherein the mammal is suffering from a lytic infection of JC polyomavirus in the brain.

13. The method of claim 1, wherein the compound or composition is conjointly administered with one or more compounds independently selected from central nervous system drugs, analgesics, narcotic agonists, narcotic antagonists, nonsteroidal anti-inflammatory/analgesic agents, behavior-modifying agents, tranquilizers/sedatives, anesthetic agents, inhalants, narcotics, reversal agents, anticonvulsants, skeletal muscle relaxants, smooth muscle relaxants, cardiovascular agents, inotropic agents, antiarrhythmic drugs, anticholinergics, vasodilating agents, agents used in treatment of shock, alpha-adrenergic blocking agents, beta-adrenergic blocking agents, respiratory drugs, bronchodilators, sympathomimetics, antihistamines, antitussives, agents for urinary incontinence/retention, urinary alkalinizers, urinary acidifiers, cholinergic stimulants, agents for urolithiasis, gastrointestinal agents, antiemetic agents, antacids, histamine H2 antagonists, gastromucosal protectants, proton pump inhibitors, appetite stimulants, GI antispasmodics-anticholinergics, GI stimulants, laxatives, saline, lubricant, surfactant, antidiarrheals, hormones/endocrine/reproductive agents, sex hormones, anabolic steroids, posterior pituitary hormones, adrenal cortical steroids, glucocorticoids, antidiabetic agents, thyroid drugs, thyroid hormones, endocrine/reproductive drugs, prostaglandins, antiinfective drugs, antiparasitics, anticoccidial agents, antibiotics, anti-tuberculosis, aminocyclitols, cephalosporins, macrolides, penicillins, tetracyclines, lincosamides, quinolones, sulfonamides, antibacterials, antifungal agents, antiviral agents, blood modifying agents, clotting agents, anticoagulants, erythropoietic agents, antineoplastics/immunosuppressives, alkylating agents, antidotes, bone/joint agents, dermatologic agents (systemic), vitamins and minerals/nutrients, systemic acidifiers, systemic alkalinizers, anti-cancer agents, or antiviral agents.

* * * * *

UNITED STATES PATENT AND TRADEMARK OFFICE
CERTIFICATE OF CORRECTION

PATENT NO. : 10,118,923 B2
APPLICATION NO. : 15/805693
DATED : November 6, 2018
INVENTOR(S) : Milton H. Werner et al.

It is certified that error appears in the above-identified patent and that said Letters Patent is hereby corrected as shown below:

In the Specification

At Column 1, Line number 18, "Contract No. 1R43AI103982-01A1 awarded" should read
-- Contract Nos. NS103695 and AI103982, awarded --

Signed and Sealed this
Seventh Day of May, 2019

Andrei Iancu
*Director of the United States Patent and Trademark Office*